(12) United States Patent
Nugent et al.

(10) Patent No.: US 8,092,524 B2
(45) Date of Patent: Jan. 10, 2012

(54) TRANSCATHETER DELIVERY OF A REPLACEMENT HEART VALVE

(75) Inventors: Alan Nugent, Dallas, TX (US); James E. Lock, Newton, MA (US)

(73) Assignee: Children's Medical Center Corporation, Boston, MA (US)

( * ) Notice: Subject to any disclaimer, the term of this patent is extended or adjusted under 35 U.S.C. 154(b) by 220 days.

(21) Appl. No.: 12/326,979

(22) Filed: Dec. 3, 2008

(65) Prior Publication Data

US 2009/0082858 A1    Mar. 26, 2009

Related U.S. Application Data

(63) Continuation of application No. 11/052,466, filed on Feb. 7, 2005, now Pat. No. 7,470,285.

(60) Provisional application No. 60/542,008, filed on Feb. 5, 2004, provisional application No. 60/575,167, filed on May 28, 2004, provisional application No. 60/610,271, filed on Sep. 16, 2004.

(51) Int. Cl.
*A61F 2/24* (2006.01)
(52) U.S. Cl. ...................................... 623/2.18
(58) Field of Classification Search .......... 623/2.1–2.19, 623/2.38
See application file for complete search history.

(56) References Cited

U.S. PATENT DOCUMENTS

| | | | |
|---|---|---|---|
| 3,570,014 A | 3/1971 | Hancock | 3/1 |
| 4,733,665 A | 3/1988 | Palmaz | 128/343 |
| 5,411,552 A | 5/1995 | Andersen et al. | 623/2 |
| 5,840,081 A | 11/1998 | Andersen et al. | 623/2 |
| 5,935,163 A | 8/1999 | Gabbay | 623/2 |
| 5,957,949 A | 9/1999 | Leonhardt et al. | 623/1.24 |
| 6,168,614 B1 | 1/2001 | Andersen et al. | 623/1 |
| 6,174,329 B1 | 1/2001 | Callol et al. | 623/1.34 |
| 6,350,282 B1 | 2/2002 | Eberhardt | 623/2.13 |
| 6,371,983 B1 | 4/2002 | Lane | 623/2.14 |
| 6,425,916 B1 | 7/2002 | Garrison et al. | 623/2.11 |
| 6,458,153 B1 | 10/2002 | Bailey et al. | 623/1.24 |
| 6,893,460 B2 | 5/2005 | Spenser et al. | 623/2.14 |
| 6,908,481 B2 | 6/2005 | Cribier | 623/2.11 |
| 7,198,646 B2 | 4/2007 | Figulla et al. | 623/900 |
| 2001/0039450 A1* | 11/2001 | Pavcnik et al. | 623/1.24 |
| 2002/0032481 A1 | 3/2002 | Gabbay | 623/1.24 |
| 2002/0188348 A1* | 12/2002 | DiMatteo et al. | 623/1.24 |
| 2003/0023303 A1* | 1/2003 | Palmaz et al. | 623/2.18 |
| 2003/0055492 A1* | 3/2003 | Shaolian et al. | 623/1.24 |
| 2003/0199963 A1 | 10/2003 | Tower et al. | 623/1.11 |
| 2004/0019374 A1 | 1/2004 | Hojeibane et al. | 623/1.13 |
| 2004/0122516 A1 | 6/2004 | Fogarty et al. | 623/2.37 |
| 2004/0186563 A1 | 9/2004 | Lobbi | 623/2.11 |

(Continued)

FOREIGN PATENT DOCUMENTS

| | | |
|---|---|---|
| WO | 98/29057 | 7/1998 |
| WO | 03/003943 | 1/2003 |

*Primary Examiner* — William H. Matthews
(74) *Attorney, Agent, or Firm* — K&L Gates LLP

(57) ABSTRACT

A replacement heart valve apparatus. The heart valve apparatus includes a stent and a valve frame having a substantially cylindrical body defining a lumen. The valve frame includes a plurality of curved wire pairs attached to the substantially cylindrical body. Each curved wire pair includes an inner curved wire and an outer curved wire. The wire frame further having a plurality of leaflets. Each leaflet is attached to a respective inner curved wire and extends over a respective outer curved wire, so as to position the body of the leaflet within the lumen of the valve frame.

10 Claims, 30 Drawing Sheets

U.S. PATENT DOCUMENTS

| | | | |
|---|---|---|---|
| 2005/0137682 A1 | 6/2005 | Justino | 623/1.24 |
| 2005/0251251 A1 | 11/2005 | Cribier | 623/2.11 |
| 2006/0052867 A1 | 3/2006 | Revuelta et al. | 623/2.18 |
| 2009/0222082 A1 | 9/2009 | Lock et al. | 623/2.11 |

* cited by examiner

Basic Anatomy of the Heart

TRANSCATHETER DELIVERY OF A REPLACEMENT HEART VALVE

RELATED APPLICATIONS

This application is a continuation of U.S. patent application Ser. No. 11/052,466, filed on Feb. 7, 2005, now U.S. Pat. No. 7,470,285 which claims the benefit of and priority to U.S. Provisional Patent Application Ser. Nos. 60/542,008, filed on Feb. 5, 2004; 60/575,167, filed on May 28, 2004; and 60/610,271, filed on Sep. 16, 2004, each owned by the assignee of the present application, and the entire content of each of which is herein incorporated by reference.

TECHNICAL FIELD

The present technology relates generally to the treatment of heart valve dysfunction and, in particular, to minimally invasive systems and methods for replacing such heart valves.

BACKGROUND IF THE INVENTION

Treatment of congenital heart disease typically requires surgical intervention, such as "open-heart" surgery during which the thoracic cavity is opened and the heart, arteries/veins and/or associated valves are repaired or otherwise treated. Postoperative complications that may appear during short and long-term patient follow-up include heart valve dysfunction. For example, tetrology of fallot is a congenital heart defect often discovered at birth, in which a baby appears blue as a result of an obstruction affecting the proper functioning of the pulmonary valve of the heart. The obstruction is often surgically removed at an early age to improve the chances that the baby will survive. The surgical procedure typically results in subsequent leaking (i.e., regurgitation) of blood through the pulmonary valve. Over the life of the patient, the regurgitation may become more severe and result in further dysfunction of the heart valve due to, for example, dilation of the heart chamber and heart valve, by the body, to compensate for the increased regurgitation.

Approximately 89,000-95,000 open-heart surgeries are performed each year to address and resolve heart valve dysfunction. The surgery requires an incision, under general anesthesia, that transects the sternum in half vertically from just below the larynx to above the diaphragm. The heart is stopped or arrested during the surgery by infusing cold saline with high potassium content. A heart-lung machine then drains the deoxygenated blood from a tube placed in the right atrium and pumps it through an oxygenator. The oxygenator has a blood gas membrane that allows carbon dioxide to leave the blood while oxygen is diffused into the blood. The oxygenated blood is then returned to the patient through a tube that runs into the aorta, above the valve. This surgery is very expensive and requires a prolonged recovery period in the hospital with additional rehabilitation once the patient is discharged. This invasive surgery also results in a large chest scar.

Heart valve dysfunction includes, for example, pulmonary regurgitation, which occurs when the heart valve in the main pulmonary artery between the heart and the lungs, is unable to prevent the backflow of blood to the right ventricle of the heart. The dysfunction of this heart valve leads to a volume load on the right ventricle and causes right ventricular dilation, which can lead to right ventricular dysfunction which is thought to contribute to ventricular tachycardia and sudden death.

Due to the long-term deleterious effects of severe pulmonary regurgitation, surgical pulmonary valve replacement is performed for patients with severe regurgitation, symptoms of exercise intolerance and/or progressive right ventricular dilation and dysfunction.

Cardiologists typically defer the valve replacement procedure as long as possible, because of: the need for a repeat open-heart surgery; the risks of surgery and cardiopulmonary bypass; and the limited lifespan of all available surgically-implanted valves. The risks associated with surgical valve replacement are particularly acute with respect to pediatric patients in that the replacement valves do not grow with the patient and thus require more frequent replacement.

Prosthetic heart valves used to replace diseased or abnormal natural heart valves are typically mechanical devices with, for example, a rigid orifice ring and rigid hinged leaflets or ball-and-cage assemblies. Prosthetic heart valves are, more recently, bioprosthetic devices that combine a mechanical assembly with biological material (e.g., human, porcine, bovine, or biopolymer leaflets). Many bioprosthetic valves include an additional support structure, such as a stent, to support the leaflets of the valve. The stent also absorbs the stresses, which would otherwise be borne by the leaflets, from the hemodynamic pressure exerted during normal heart operation.

Heart valve replacement, typically, involves the surgical implantation of the valve prosthesis during open heart surgery and requires the use of a heart and lung machine for external circulation of the blood as the heart is stopped and the artificial valve prosthesis is sewed in. Valve replacement surgery is thus very demanding on the patient's body and may, therefore, not be a viable technique for patients that are physically weak due to age or illness. Accordingly, it is desirable to develop a heart valve replacement apparatus and procedure that is minimally invasive and does not have the morbidity of a re-operation.

SUMMARY

Replacement heart valves and supporting structures, made and used in accordance with the disclosed technology, enable cardiologists to implement minimally invasive procedures that avoid the morbidity of a re-operation.

In one embodiment, an apparatus made in accordance with the disclosed technology enables the transcatheter delivery of a replacement heart valve. The apparatus includes an introducing catheter, a stent and a valve frame. The stent is adapted to receive the valve frame and is deployable within an anatomical lumen of the heart via the introducing catheter prior to the stent receiving and supporting the valve frame. In one aspect, the stent has a barrel or sinus shape when opened so as to mimic the physiological shape of a human heart valve. In another aspect, a balloon catheter expands the stent once it is withdrawn from the introducing catheter. In another aspect, the stent self-expands once it is withdrawn from the introducing catheter.

In one embodiment, a stent made in accordance with the disclosed technology enables the transcatheter delivery of a valve frame. The stent includes a plurality of securing structures or materials (e.g., sutures or adhesive), where each such securing structure or material is adapted to receive and support one of a plurality of valve frames.

The two-part methodology discussed above, where the stent is deployed first and the valve frame is deployed and affixed to the stent second, enables the introducing catheter to be a relatively small French size and reduces the distortion of the replacement heart valve during implantation. The stent also enables multiple valve frame replacements without replacing the stent and maintains precise valve frame alignment relative to the stent when deployed within the anatomical lumen.

In one embodiment, the disclosed technology enables a minimally invasive method of implanting a replacement heart valve. In one aspect, a valve assembly is deployed within an anatomical lumen of the heart via an introducing catheter. The valve assembly is a unitary body possessing the functionality of both a stent and a valve frame.

In general, in another aspect, the invention involves a prosthetic valve for altering the flow of blood through a blood vessel of a heart. The valve includes a stent that has a first, generally cylindrical body. The first, generally cylindrical body has a first mesh and defines a first lumen. The first lumen extends along the length of the first, generally cylindrical body. The valve also has a valve frame that is positionable co-axially within the first lumen of the stent. The valve frame has a second, generally cylindrical body that has a second mesh. The second, generally cylindrical body defines a second lumen and a plurality of leaflets. The second lumen extends along the length of the second, generally cylindrical body.

Embodiments of this aspect of the invention can include the following features. The first, generally cylindrical body of the prosthetic valve can define a region that protrudes from the first, generally cylindrical body. The region can be a plurality of regions. The plurality of leaflets of the prosthetic valve can be located at one end of the second, generally cylindrical body.

In general, in another aspect, the invention involves a prosthetic valve for altering the flow of blood through a blood vessel of a heart. The valve includes a valve assembly that has a generally cylindrical body. The generally cylindrical body has a mesh and a plurality of leaflets. The generally cylindrical body defines a lumen that extends along the length of the generally cylindrical body.

Embodiments of this aspect of the invention can include the following features. The generally cylindrical body of the prosthetic valve can define a region that protrudes from the generally cylindrical body. The region can be a plurality of regions. The plurality of leaflets of the prosthetic valve can be located at one end of the generally cylindrical body.

In another aspect, an apparatus made in accordance with the disclosed technology enables the transcatheter delivery of a replacement heart valve. The apparatus includes a stent having a bulbous proximal end and a distal end with a neck extending therebetween, the distal end of the neck defining a tapered portion. Also included in the device is a valve frame receivable within a lumen of the stent where a distal end of the valve frame is engageable with the tapered portion of the stent and where valve members of the valve frame are engageable with the bulbous proximal end of the stent.

In another embodiment the invention relates to a replacement heart valve apparatus including a stent and a valve frame. The valve frame has a substantially cylindrical body defining a lumen and having a plurality of curved wire pairs attached at one end of the substantially cylindrical body. Each curved wire pair includes an inner curved wire and an outer curved wire. The wire frame has a plurality of leaflets. Each leaflet is attached to a respective inner curved wire and extends over a respective outer curved wire, to be positioned within the lumen of the valve frame.

These and other objects, along with the features of the present invention herein disclosed, will become apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis generally being placed upon illustrating the principles of the invention. In the following description, various embodiments of the present invention are described with reference to the following drawings, in which.

DETAILED DESCRIPTION

Figure 1:
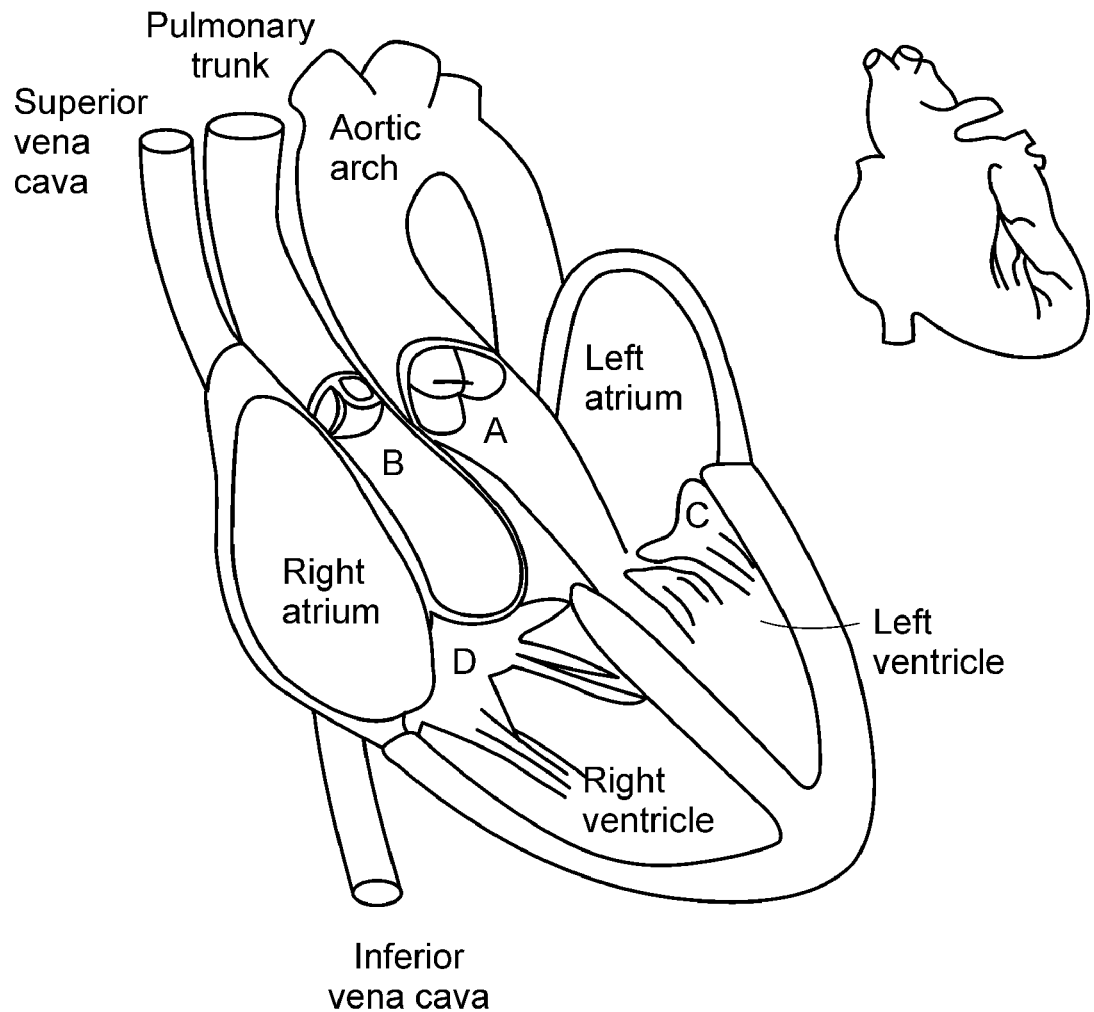
FIG. 1 is a partially broken-away view of a heart showing the typical location of various heart valves.

In brief overview and with reference to FIG. 1, the heart has four chambers and is located in the middle of the chest with a slight tilt toward the left side. Deoxygenated blood (containing low oxygen) returns from the entire body via the superior and inferior branches of the vena cava emptying into the right atrium. During diastole, or the relaxation phase of the cardiac cycle, pressure in the right ventricle falls from between about 20 mm Hg and about 30 mm Hg to between about 5 mm Hg and about 10 mm Hg. The pressure gradient formed between the right atrium and right ventricle, plus the contraction of the atrium, causes forward flow of blood through the tricuspid valve into the right ventricle. The flow of blood through the tricuspid valve thereby fills the right ventricle with blood. During systole, the pumping phase of the cycle, the right ventricle starts to contract, increasing intraventricular pressure. This causes the tricuspid valve to snap shut and the cusps of the pulmonary valve to open. Blood then flows out of the right ventricle through the pulmonary artery into the lungs where oxygenation occurs and carbon dioxide is removed.

The cycle of blood flow starts against with relaxation of the right ventricle. Because the diastolic pressure (e.g., less than about 5 mm Hg) in the right ventricle is lower than the pulmonary artery pressure (e.g., about 10 mm Hg) the pulmonary valve closes and prevents regurgitation. Simultaneously with the fall in the pressure in the right ventricle, the tricuspid valve opens and again fills the right ventricle.

Once the blood has been oxygenated, it flows into the left side of the heart via the pulmonary veins into the left atrium. It is during diastole that blood flows through the mitral valve into the left ventricle. During systole, the pressure in the left ventricle causes the mitral valve leaflets to close and the aortic valve to open. The blood flows out of the aorta for circulation throughout the body.

The geometry and circuitry of the two sides of the heart are similar; however the function of each is different. The right side pumps blood only to the lungs for gas exchange. The left side pumps blood to the entire body. The left side generates pressures three to four times greater than the right side.

As discussed, there are four valves within the human heart, located at the exit of each chamber. In order of blood flow, they are the tricuspid (right atrium), pulmonary (right ventricle), mitral (left atrium) and aortic valves (left ventricle). Due to the higher-pressure gradient, the mitral and aortic valves are subject to greater fatigue and/or risk of disease. The aortic and pulmonary valves are similar anatomically and are referred to as semi-lunar valves.

Figure 2A:
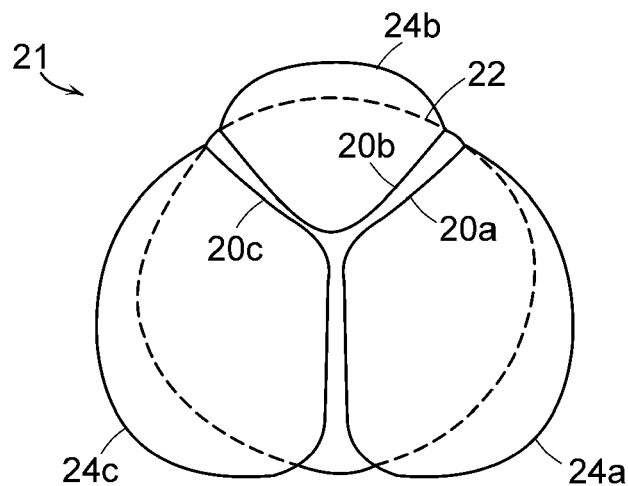
FIG. 2A is a top-view of a natural heart valve.
Figure 2B:
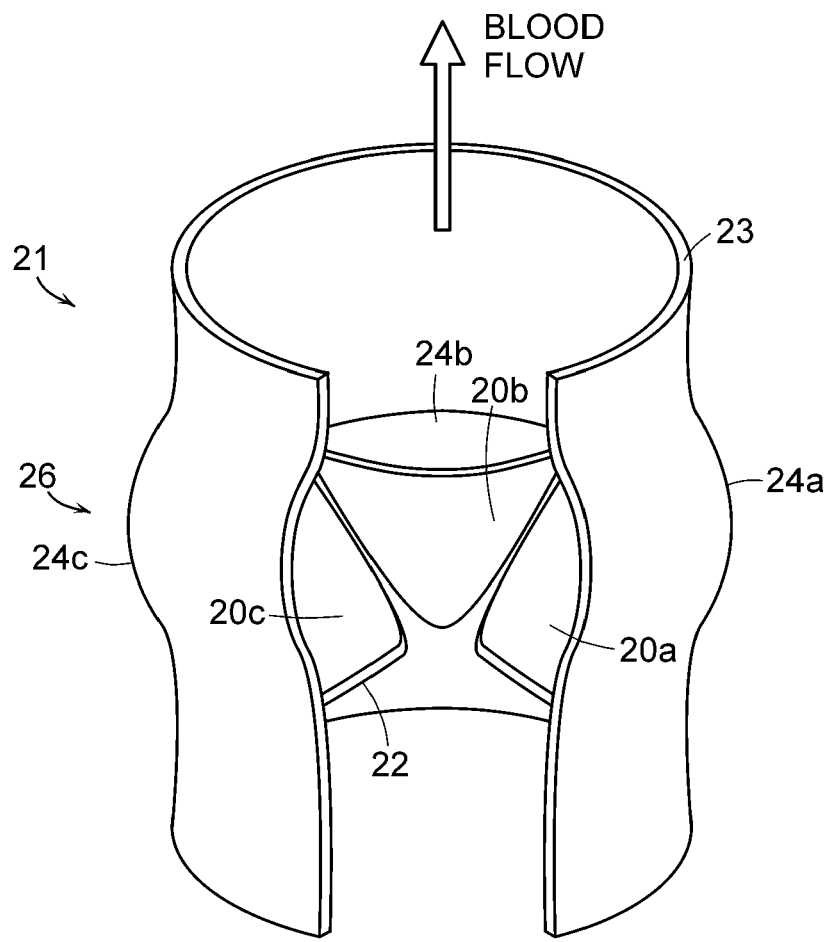
FIG. 2B is a partially broken-away isometric view of a natural heart valve.

As illustrated in FIGS. 2A and 2B, an aortic valve 21 is a semi-lunar valve, named because of the partial moon-like shape of its three cusps 20a, 20b and 20c (generally 20). The three cusps 20a, 20b and 20c are soft tissue structures attached to a wall 23 of the aortic valve 21 in an area designated as the annulus 22. During the contraction phase of systole, the three cusps 20a, 20b and 20c are pushed back against the wall 23 of the aorta and blood flows (as illustrated in FIG. 2B) through the aortic valve 21. During diastole or relaxation of the ventricle, the pressure in the left ventricle falls and blood begins to flow backward (in the opposite direction to the blood flow indicated in FIG. 2B). During diastole, the left ventricular pressure falls and when the pressure is below the relaxation pressure of the aorta, the aortic valve closes (the cusps 20a, 20b and 20c fall away from the wall 23 and close), thereby eliminating backward flow of the blood.

A unique feature of the aortic valve 21 is the presence of aortic sinuses in the region of the valve referred to as the root 26. There are three sinuses 24a, 24b and 24c that have an orifice at each of the cusps 20a, 20b and 20c, respectively. These barrel-shaped regions or orifices located in the sinuses 24a, 24b and 24c affect the fluid dynamics of blood in the area of the aortic valve 21 and may contribute to the opening and closing of the cusps 20a, 20b and 20c of the aortic valve 21. Two of the cusps are named for branches of the main coronary arteries for which the cusps act as openings (i.e., the left and right coronary sinuses) and the third sinus is named the non-coronary sinus. The three corresponding cusps 20a, 20b and 20c are named in a similar fashion.

The disclosed technology mitigates the potential complications of invasive surgery, by applying minimally invasive techniques to, for example, replace a damaged natural heart valve with a replacement heart valve. In one embodiment, a supporting structure, such as a stent or scaffold, is deployed at a preselected position within an anatomical lumen of the heart via an introducing catheter. The term "stent" and "docking station" are hereafter used to broadly refer to all types of supporting structures and scaffolds. The replacement heart valve is then inserted into the deployed stent using the same catheter or, alternatively, a second catheter. The stent and/or valve assembly include attachment means (e.g., sutures or adhesive) to hold securely the valve assembly in a desired orientation and alignment relative to the stent. The two-part deployment of the stent and the heart valve enable the use of smaller catheters because the inner diameter of the catheter need not accommodate, at the same point in time of the procedure, the compressed volume of both a stent and a valve assembly.

Figure 3A:
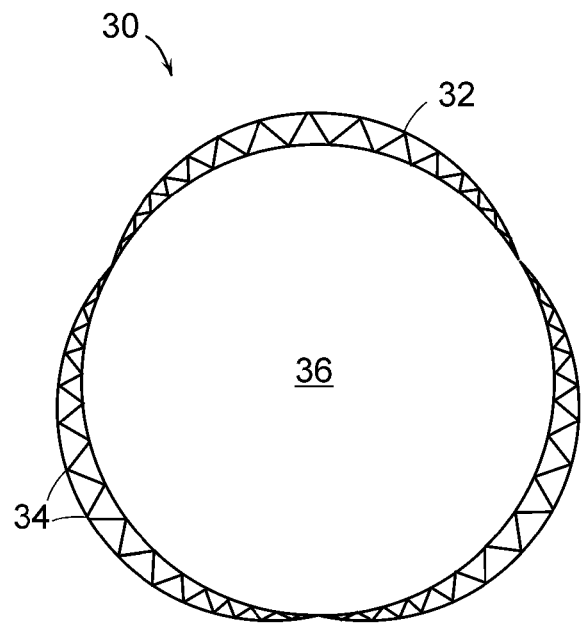
FIG. 3A is a top-view of an embodiment of a stent according to the invention.
Figure 3B:
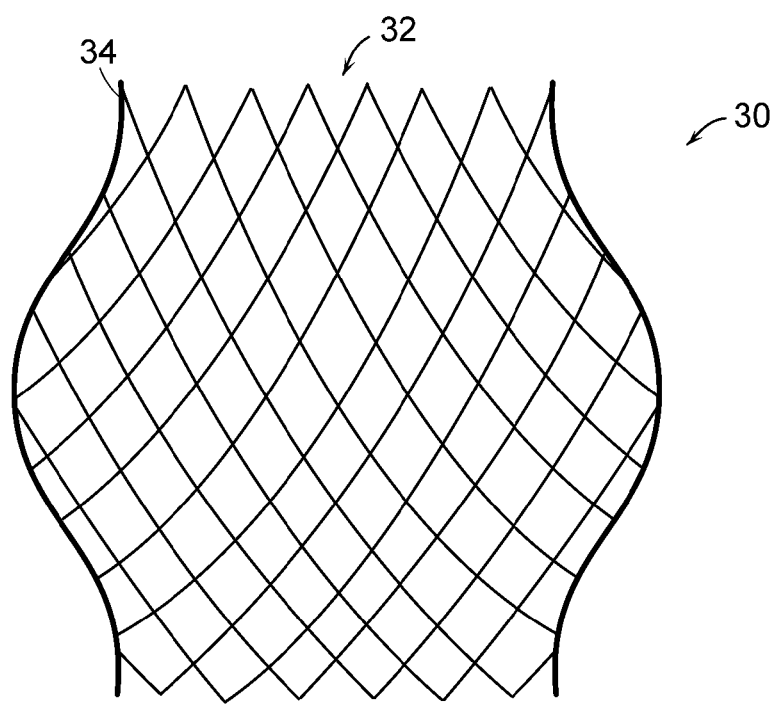
FIG. 3B is a side-view of the stent of FIG. 3A.

As shown in FIGS. 3A and 3B, one embodiment of a stent 30 according to the invention is made of a shape memory material. The stent 30 defines a generally cylindrical body that has a wall 34 that is constructed from a mesh 32. The wall 34 defines a lumen 36. The mesh 32 is constructed from, for example, wires or strips of shape memory material. By way of example, the shape memory material might be nickel-titanium wire sold under the product name Nitinol. The nickel-titanium wire, when properly manufactured, exhibits elastic properties that allow for the wire to be manipulated (e.g., bent) by an operator and then returned to, substantially, the same shape the wire possessed prior to it being manipulated. The wire returns to, substantially, the same shape the wire possessed prior to it being manipulated, for example, when the operator heats the wire or, alternatively, when the operator removes the forces applied to bend the wire. In this embodiment, the stent 30 approximates the form of a cloverleaf to closely conform, for example, to the cloverleaf-like shape (associated with the three sinuses of a natural heart valve) of the location in a heart where a defective heart valve has been surgically removed.

The stent 30 could, alternatively, be any geometric shape (e.g., cylindrical, conical, spherical or barrel-like) that is compatible with the placement of the stent 30 within, for example, a lumen of the heart. The stent 30 could be manufactured using alternative materials (e.g., stainless steel alloys, molybdenum alloys or pyrrolitic carbon) that are compatible with placement in the body, that possess desirable material wear properties and/or that have a minimal risk of causing infection in the body of the patient.

Figure 4A:
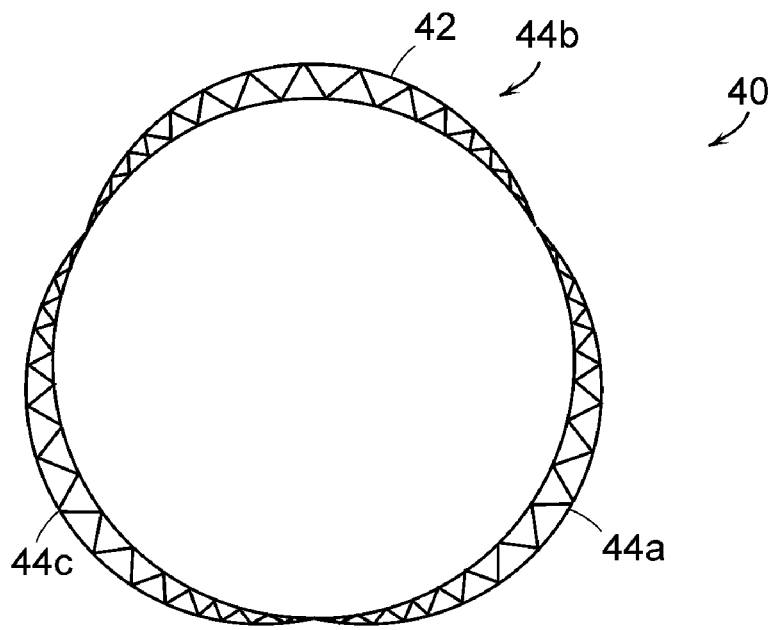
FIG. 4A is a top-view of an embodiment of a valve frame according to the invention.
Figure 4B:
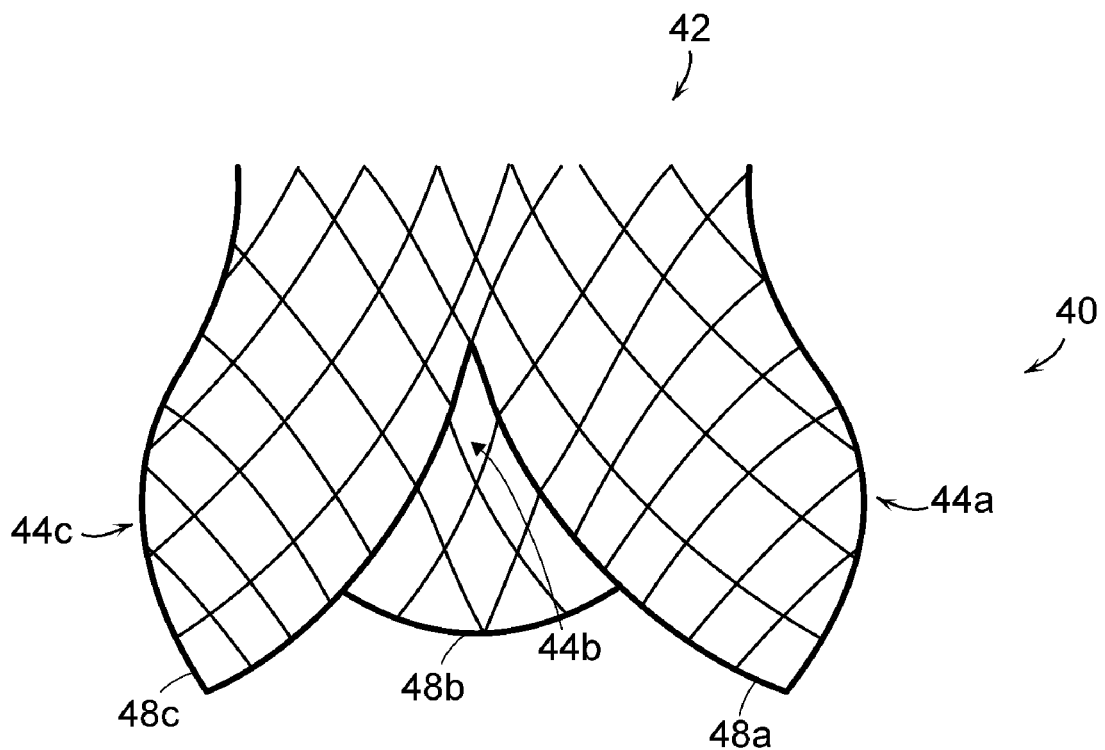
FIG. 4B is a side-view of the valve frame of FIG. 4A.

FIGS. 4A and 4B illustrates one embodiment of a valve frame 40 in deployed form (i.e., not constrained by, for example, a wall of a lumen of a catheter used to introduce the valve frame 40 into the body). The valve frame 40 may be deployed within a stent, such as the stent 30 of FIG. 3B. The valve frame 40 is made of a shape memory material. The valve frame 40 defines a, generally, cylindrical body that is constructed from a mesh 42. The mesh 42 may be constructed from wires or strips of a shape memory material. The valve frame 40 also has three valve members 44a, 44b and 44c. The valve members 44a, 44b and 44c have a free end 48a, 48b and 48c, respectively. The valve frame 40 could, alternatively, be any geometric shape (e.g., cylindrical, conical, spherical or barrel-like) that is compatible with the placement of the valve frame 40 within a stent, such as the stent 30 of FIG. 3B.

Figure 5A:
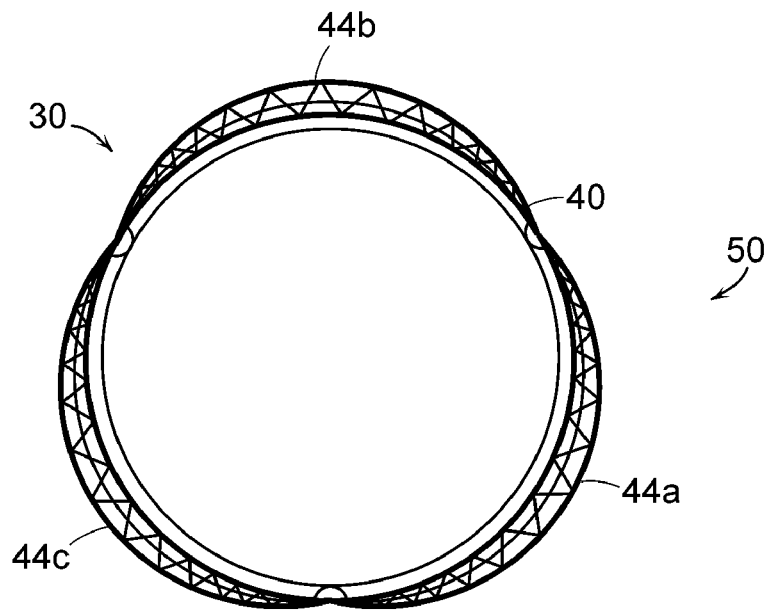
FIG. 5A is a top-view of the valve frame of FIG. 4A located within a lumen of the stent of FIG. 3A.
Figure 5B:
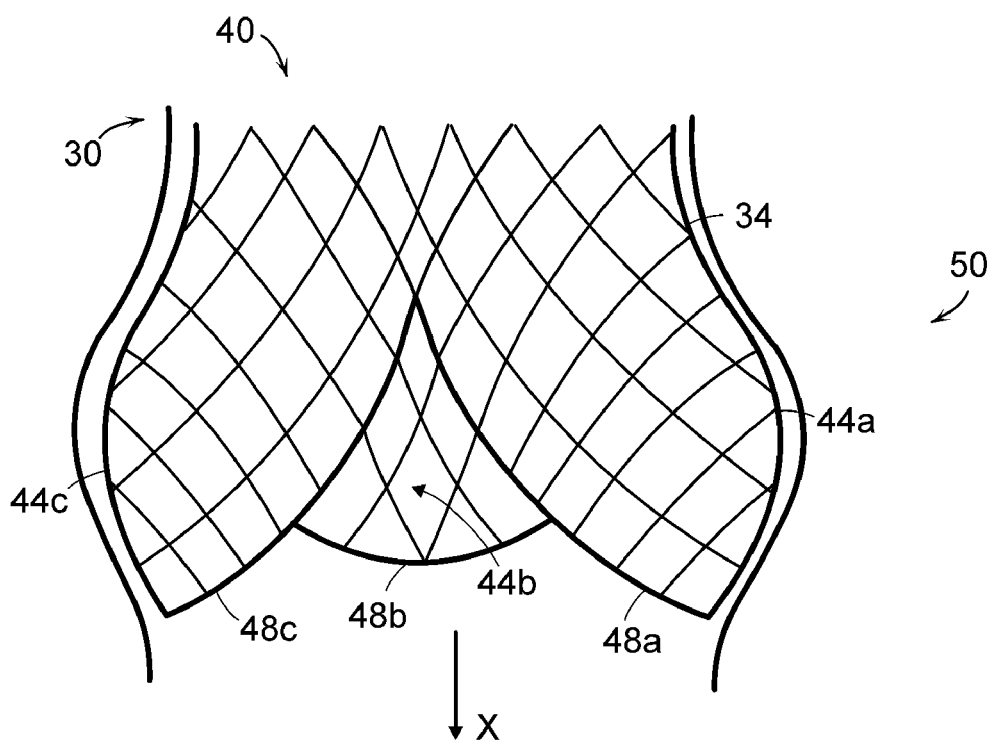
FIG. 5B is a side-view of the valve frame and stent of FIG. 5A.
Figure 5C:
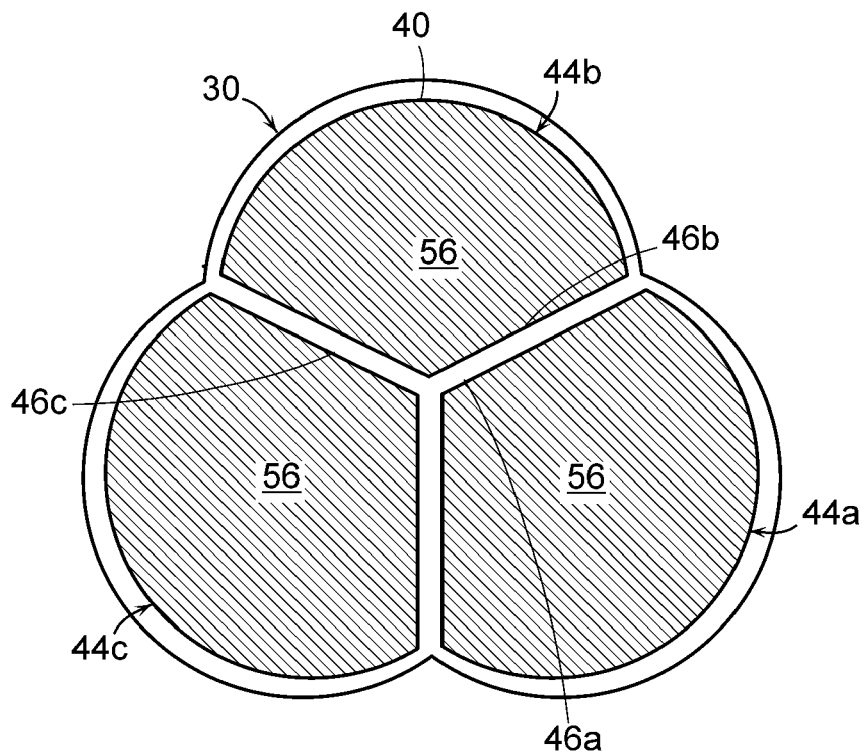
FIG. 5C is a top-view of the valve frame and stent of FIG. 5A with the members of the valve frame covered with a cover material and free ends of the cover material located away from the wall of the stent.
Figure 5D:
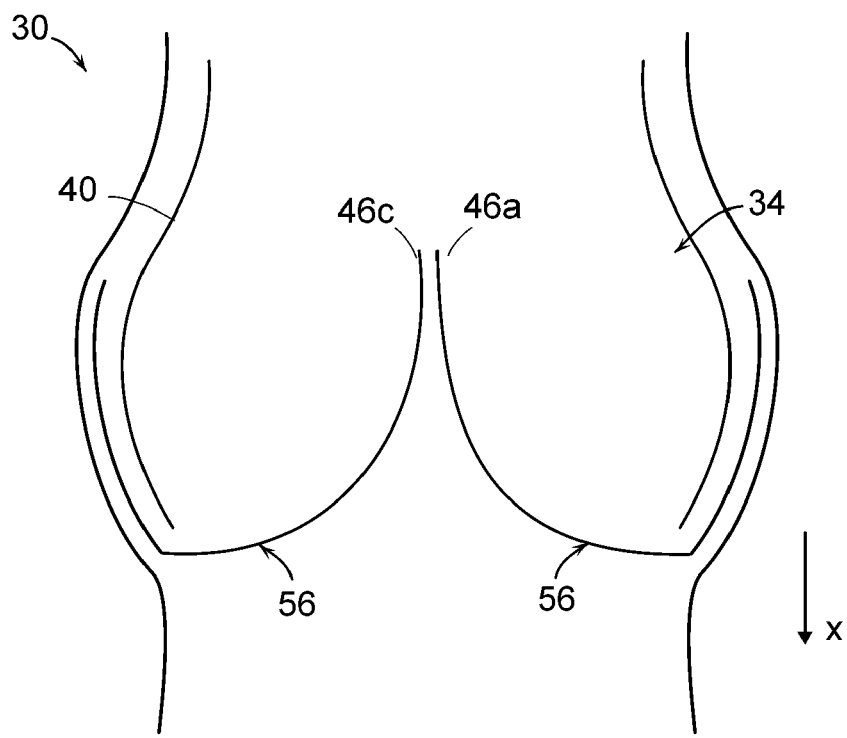
FIG. 5D is a cross-sectional view of the valve frame and stent of FIG. 5C.

As shown in FIGS. 5A and 5B, the valve frame 40 may be deployed within the lumen 36 of the stent 30 thereby creating a valve assembly 50. In one embodiment, the valve assembly 50 may be deployed within a human heart to replace a natural heart valve that may not function properly. The valve frame 40 would be manufactured to ensure that the valve frame 40 would maintain a desired (e.g., fixed) placement with respect to the stent 30 when the valve frame 40 and the stent 30 are located within the heart of a patient and subjected to the flow of blood through the valve assembly 50. Referring now to FIGS. 5C and 5D, the valve members 44a, 44b and 44c would be coated, typically, with a cover material 56 (e.g., a biocompatible material, such as, silicon rubber or bovine, porcine or human tissue that is chemically treated to minimize the likelihood of rejection by the patient's immune system). The coated valve members 44a, 44b and 44c would be capable of functioning similarly to the cusps 20a, 20b and 20c of FIG. 2B. The cover material 56 may be a bio-engineered material that is capable of being applied to the valve members 44a, 44b and 44c. The cover material 56 would be applied to the valve frame 40 prior to deployment of the valve frame 40 into the body. The cover material 56 has three free ends 46a, 46b and 46c corresponding to valve members 44a, 44b and 44c, respectively. The free ends 46a, 46b and 46c also are referred to as leaflets. After placement of the valve frame 40 within the stent 30 (located within the body) the cover material 56 applied to the valve members 44a, 44b and 44c is capable of, generally, obstructing the flow of blood in the positive direction along the X-axis. The free ends 46a, 46b and 46c move away from the inner wall 34 of the stent 30, thereby limiting the flow of blood in the positive direction along the X-axis.

Figure 5E:
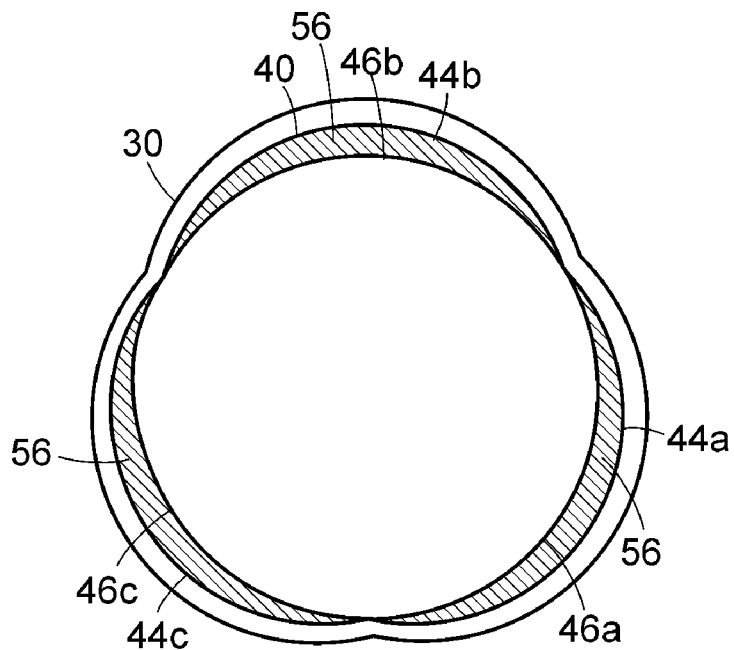
FIG. 5E is a top-view of the valve frame and stent of FIG. 5C with the free ends of the cover material located towards the wall of the stent.
Figure 5F:
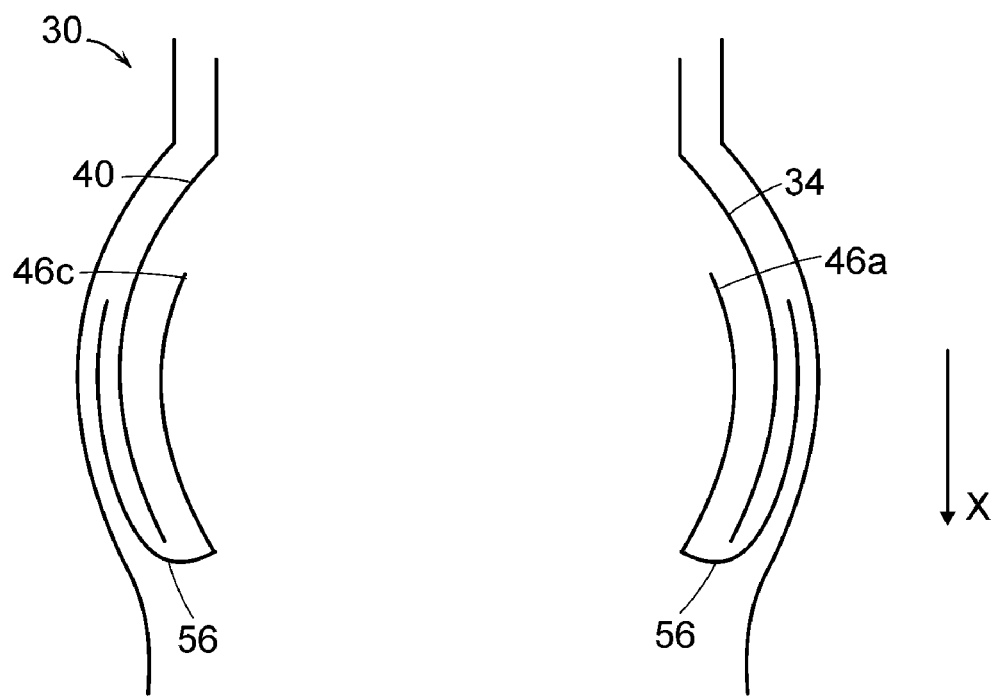
FIG. 5F is a cross-sectional view of the valve frame and stent of FIG. 5E.

However, as blood flows in the negative direction along the X-axis, referring now to FIGS. 5E and 5F, the free ends 46a, 46b and 46c of the cover material 56 move towards the inner wall 34 of the stent 30. The free ends 46a, 46b and 46c, thereby substantially restrict the flow of blood through the valve assembly 50. In this manner, the valve assembly 50 approximates the functioning of a natural heart valve of the body by allowing blood to flow in the negative direction along the X-axis.

Figure 13A:
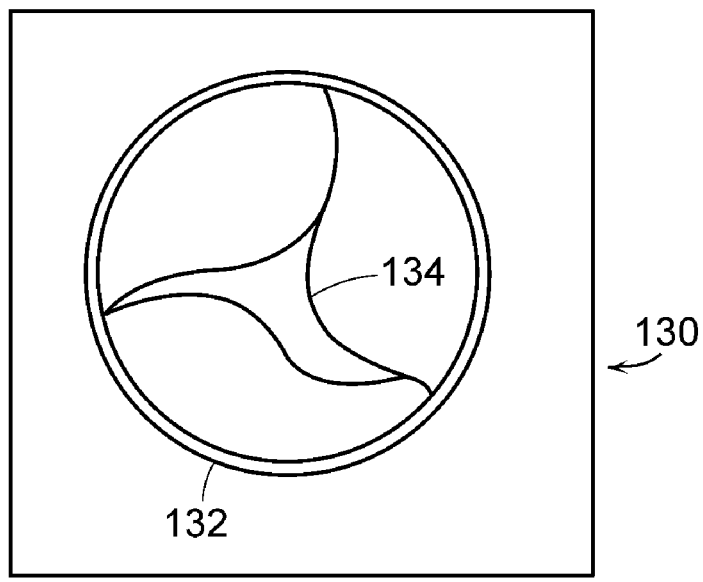
FIG. 13A is a top view of a digital image of a model of a valve frame, such as the valve frame of FIG. 5C.
Figure 13B:
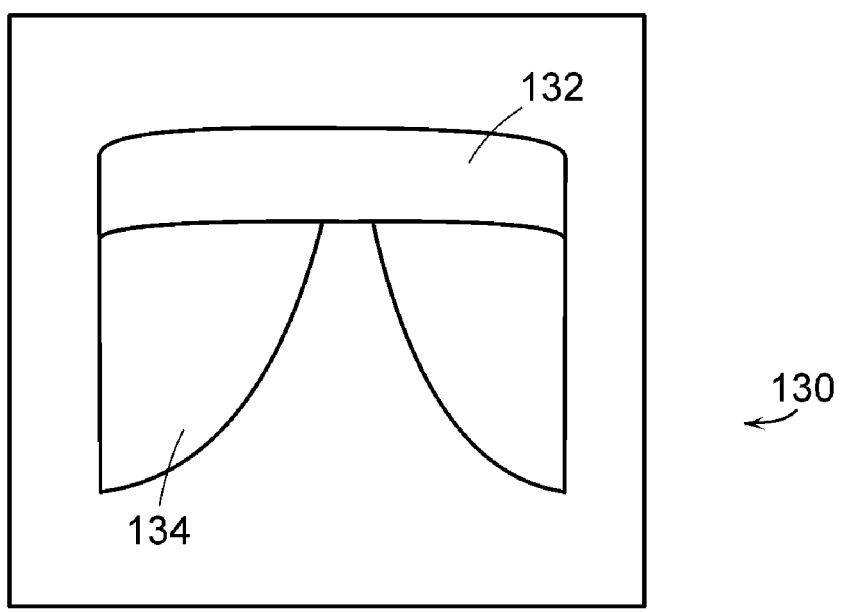
FIG. 13B is a side-view of a digital image of a model of a valve frame, such as the valve frame of FIG. 5C.

FIGS. 13A and 13B are digital images of a model 130 of a valve frame, such as the valve frame 40 of FIG. 5C. For clarity of illustration purposes the valve frame model 130 is constructed from a tube 132 and a silicon rubber cover material 134. The valve frame model 130, referring now to FIG. 13B, is cylindrical in shape. The valve frame model 130, alternatively, could be any geometric shape as described previously herein.

Figure 6:
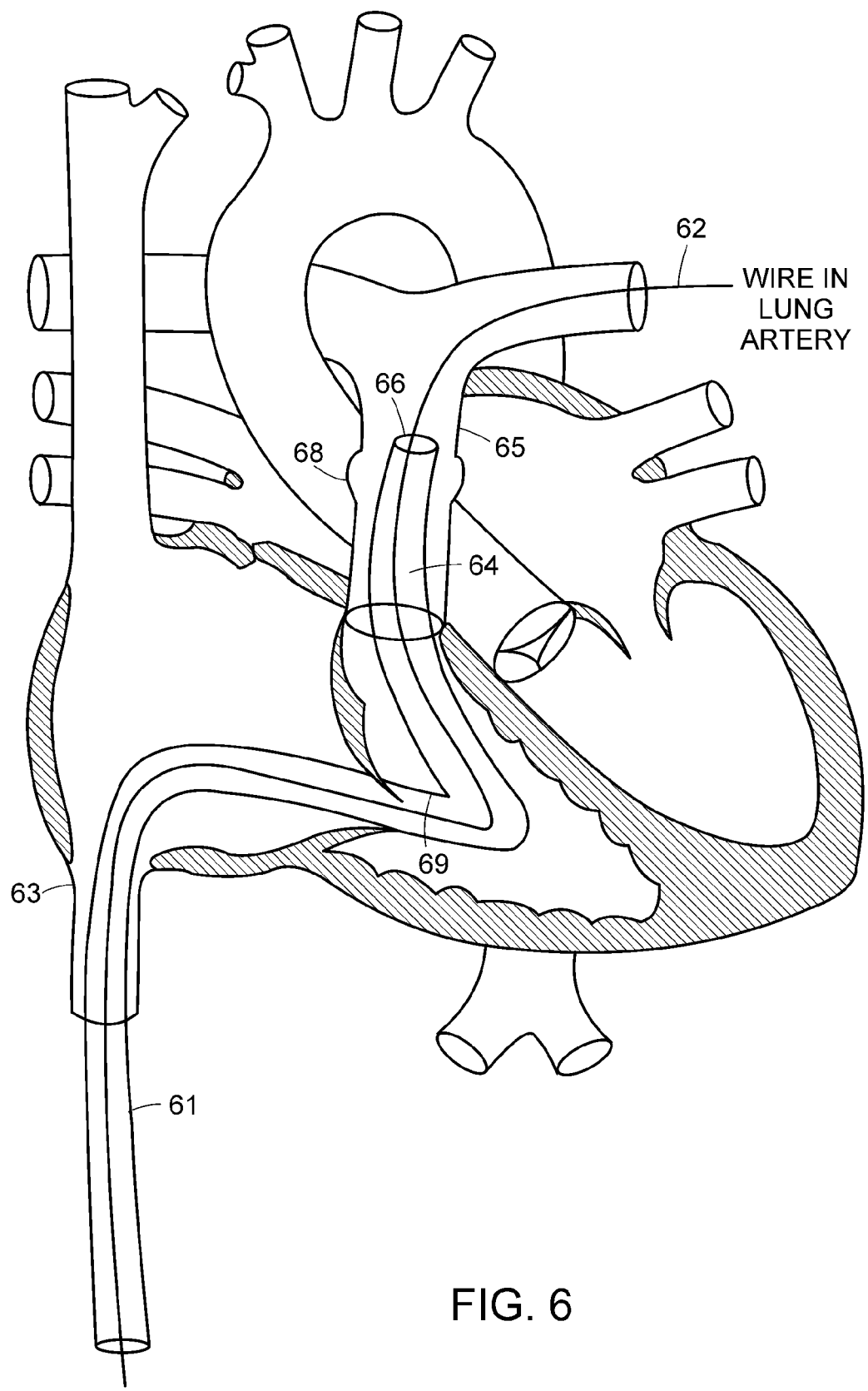
FIG. 6 is a partially broken-away view of a heart subsequent to insertion of an introducing catheter into the heart.

In more detail and with reference to FIG. 6, method steps associated with introducing an embodiment of the invention are described. An introducing catheter 61 is delivered via a femoral vessel to the inferior vena cava 63 by means of a guidewire 62 to a preselected position 68 in an anatomical lumen 65 of the heart. The preselected position 68 may be in proximity to the original location of a natural heart valve. The introducing catheter 61 has an inner wall 69 that defines a lumen 64 through which the guidewire 62 is passed. The introducing catheter 61 has an opening 66 out of which the guidewire 62 is extended. In one embodiment, the leaflets of the natural heart valve are removed prior to the insertion of the introducing catheter 61 into the heart by resecting the leaflets intravenously (e.g., by inserting a cutting and grasping device via a catheter to cut and remove the leaflets).

Figure 7:
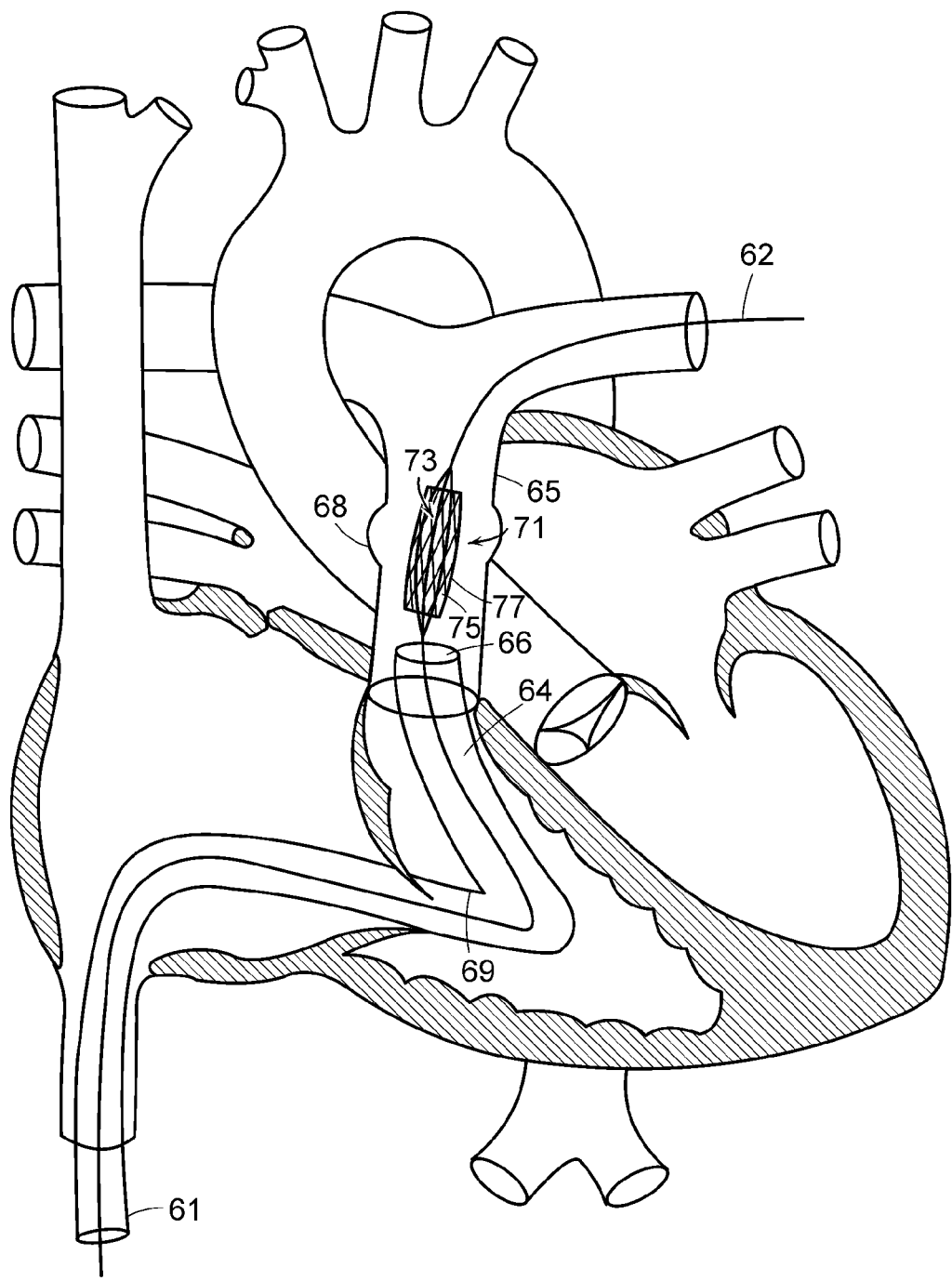
FIG. 7 is a partially broken-away view of the heart of FIG. 6 subsequent to placement of a stent and balloon in a predetermined location of an anatomical lumen of the heart.

In another embodiment, the natural heart valve remains within the heart. With reference also to FIG. 7, a stent/balloon combination 71 is inserted into the introducing catheter 61 and is guided to the preselected position 68 using the guidewire 62. The combination 71 is then deployed from the confines of the introducing catheter 61 and is located within the anatomical lumen 65. The stent/balloon combination 71 includes a balloon 73 located within a lumen 75 of a stent 77. In one embodiment, the stent/balloon combination 71 is positioned within the introducing catheter 61 prior to inserting the introducing catheter 61 into the anatomical lumen 65. In another embodiment, the stent/balloon combination 71 is inserted into the introducing catheter 61 after the opening 66 of the introducing catheter 61 has been located at the preselected position 68. In one embodiment, the preselected position 68 corresponds to the sinus-shaped region of the anatomical lumen 65. In another embodiment, the preselected position 68 corresponds to a region within the anatomical lumen 65 that is in substantial proximity to the original position of the natural heart valve.

Figure 8:
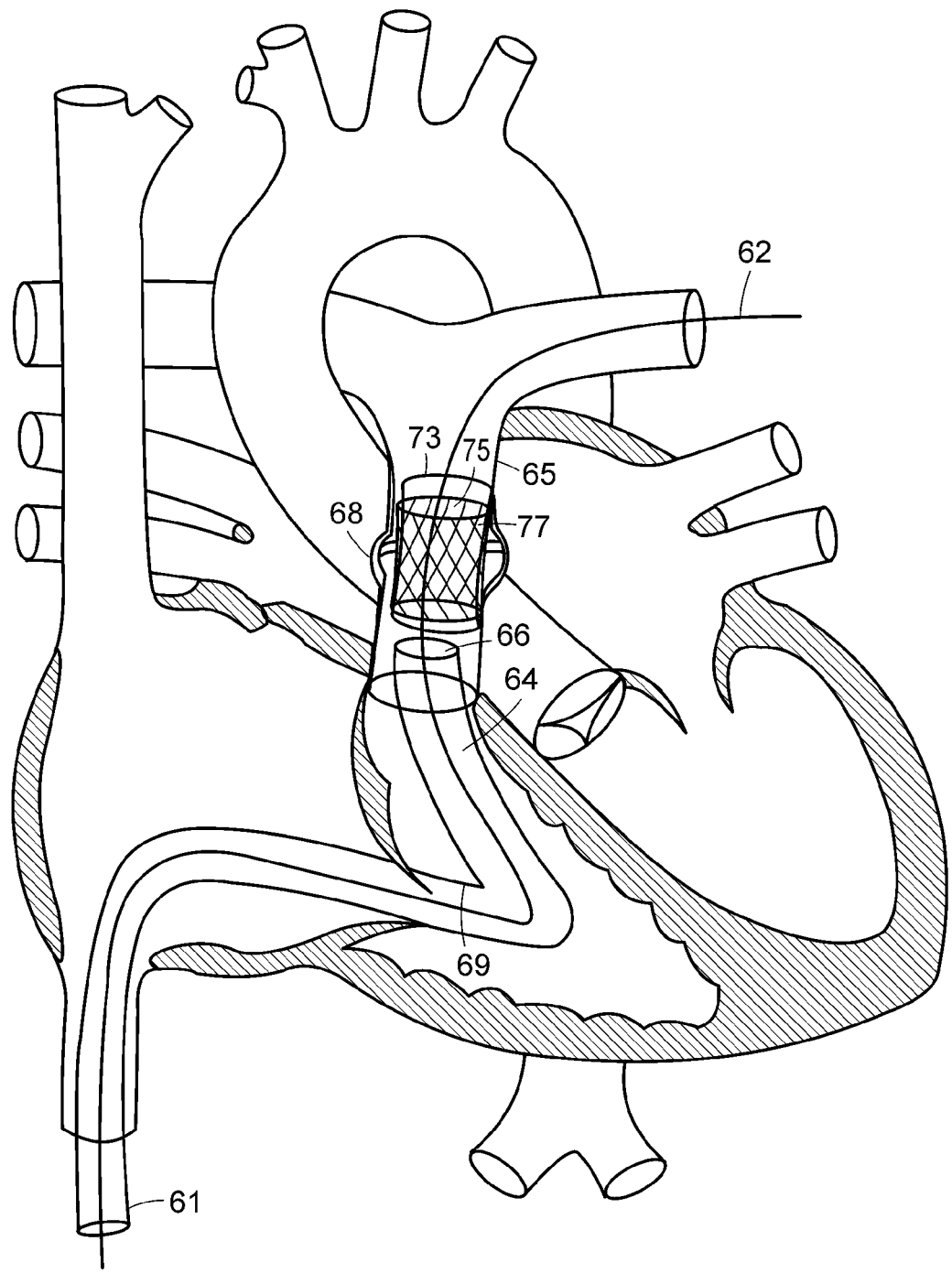
FIG. 8 is a partially broken-away view of the heart of FIGS. 6 and 7 subsequent to the stent and balloon being deployed in the heart.

The balloon 73 of the deployed stent/balloon combination 71 is then inflated, referring now to FIG. 8, thereby expanding the stent 77 to a predetermined configuration and size. The expanded configuration of the stent 77 conforms to the sinus-shaped region of the anatomical lumen 65. In one embodiment, the size and shape of the sinus-shaped stent 77 is sufficient to hold the stent 77 in a substantially fixed position and orientation within the anatomical lumen 65. In a further embodiment, the sinus-shaped stent 77 includes elements (e.g., sutures, hooks, spikes or tack tips) that attach to the interior walls of the anatomical lumen 65 so as to more rigidly hold the stent 77 in a fixed position.

In another embodiment, the stent 77 is made of a shape memory material, such as a nickel-titanium wire, and self-expands when it is removed from the confines of the introducing catheter 61. Subsequent to deploying the stent 77 from the introducing catheter 61 the stent 77 expands to a predetermined size and shape because there are no longer any constraining forces (e.g., by the inner wall 69 of the introducing catheter 61) applied to the stent 77.

Figure 9:
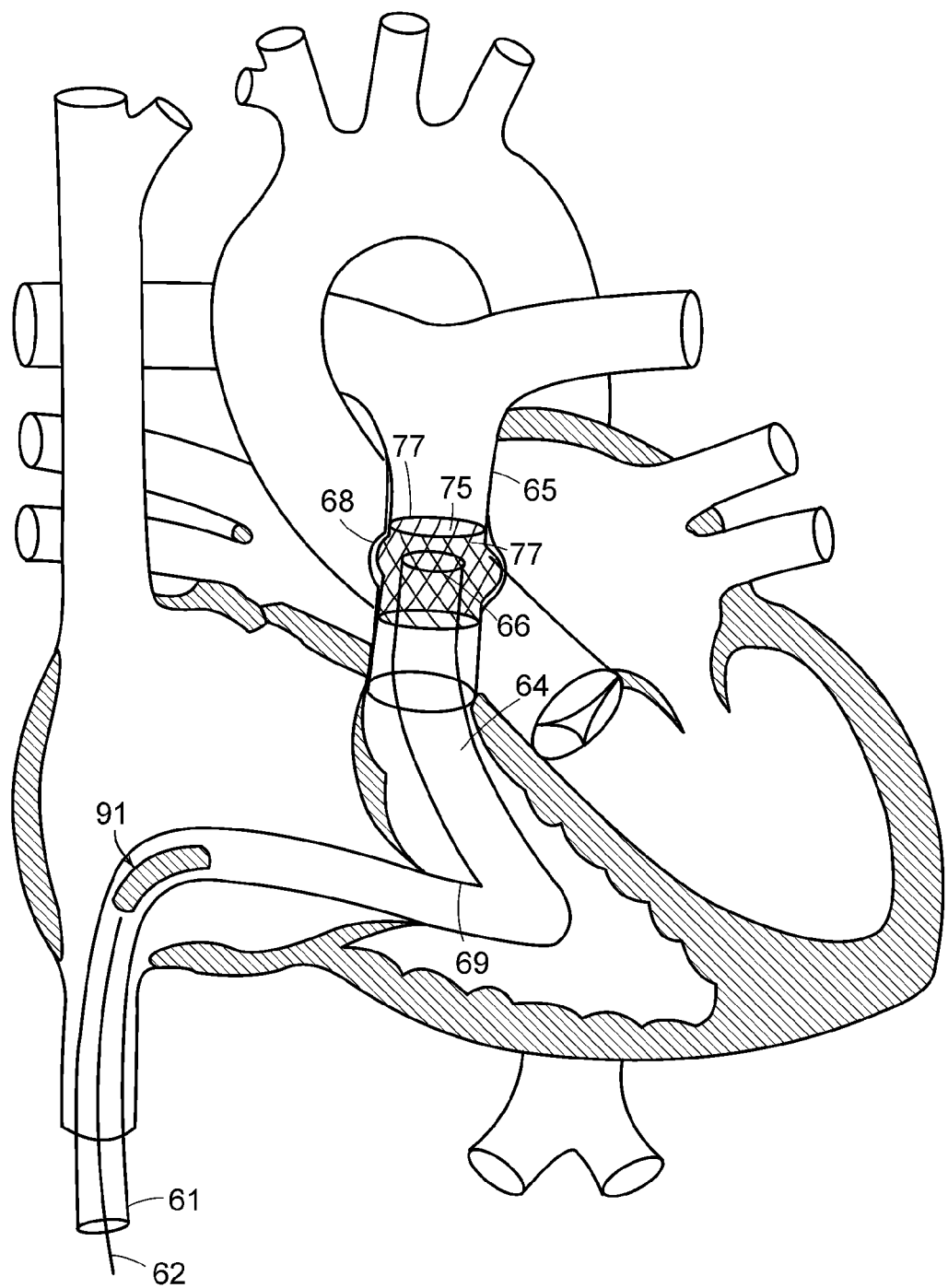
FIG. 9 is a partially broken-away view of the heart of FIGS. 6, 7 and 8 subsequent a valve frame being introduced into the introducing catheter.
Figure 10:
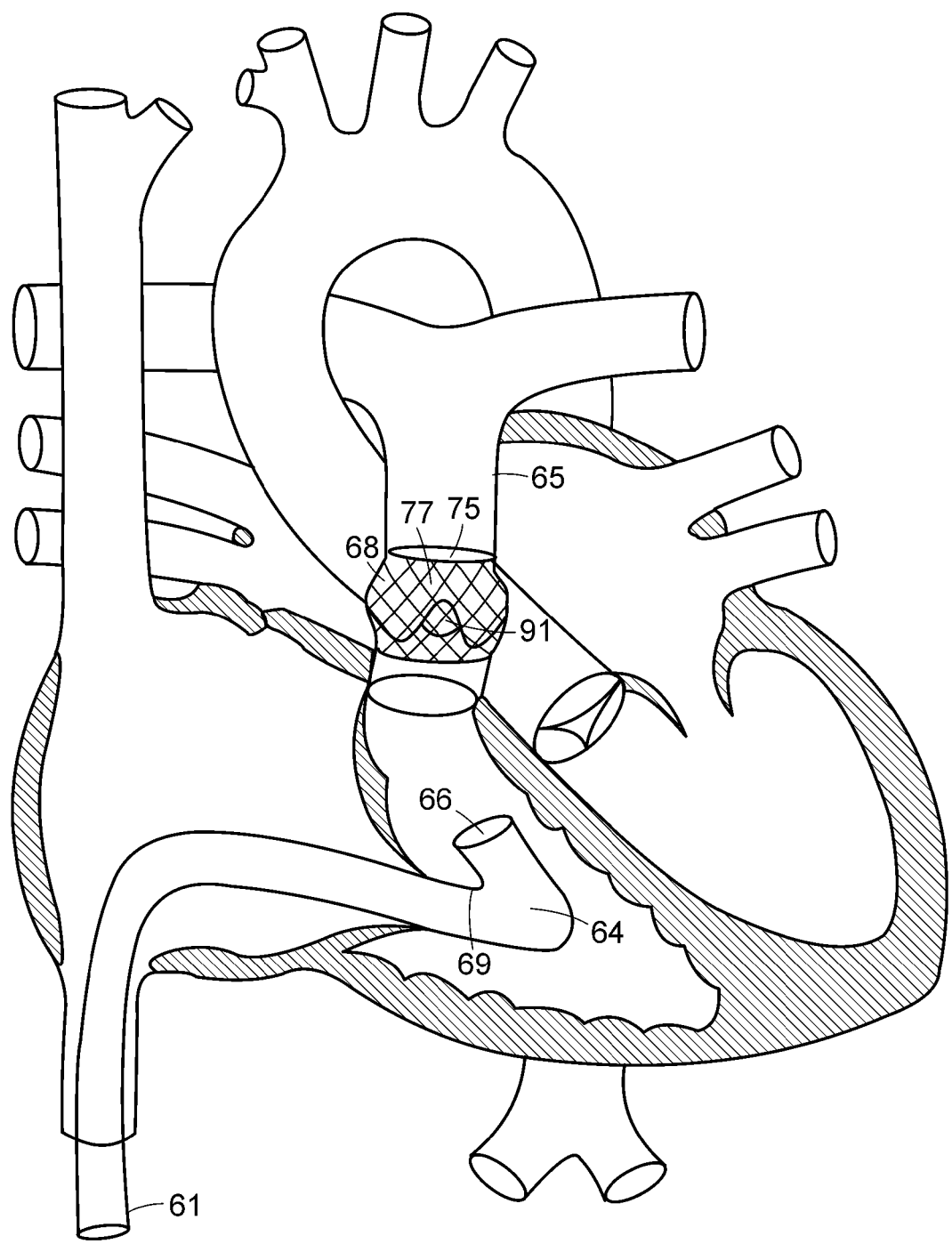
FIG. 10 is a partially broken-away view of the heart of FIGS. 6, 7, 8 and 9 subsequent to the deployment of the valve frame within the stent.

Referring now to FIG. 9 and FIG. 10, a valve frame 91 is compressed and inserted into the introducing catheter 61 and the valve frame 91 is guided to the catheter orifice 66 and deployed into the lumen 75 of the expanded stent 77. By way of example, in one embodiment the valve frame 91 may be the valve frame 40 of FIG. 4A. The valve frame 91 expands upon being deployed from the introducing catheter 61 and assumes substantially the same size and shape as the lumen 75 of the expanded stent 77. The stent 77 and/or valve frame 91 have attachment means that serve to align and fix the valve frame 91 in the predetermined position 68 within and with respect to the stent 77. Referring now to FIG. 10, the introducing catheter 61 is then removed from the anatomical lumen 65 and the operation of the replacement valve is subsequently monitored.

Figure 11A:
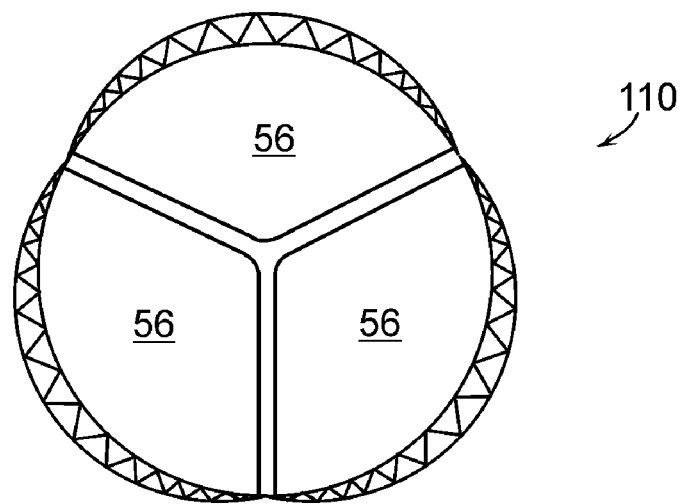
FIG. 11A is a top-view of an embodiment of a valve assembly according to the invention.
Figure 11B:
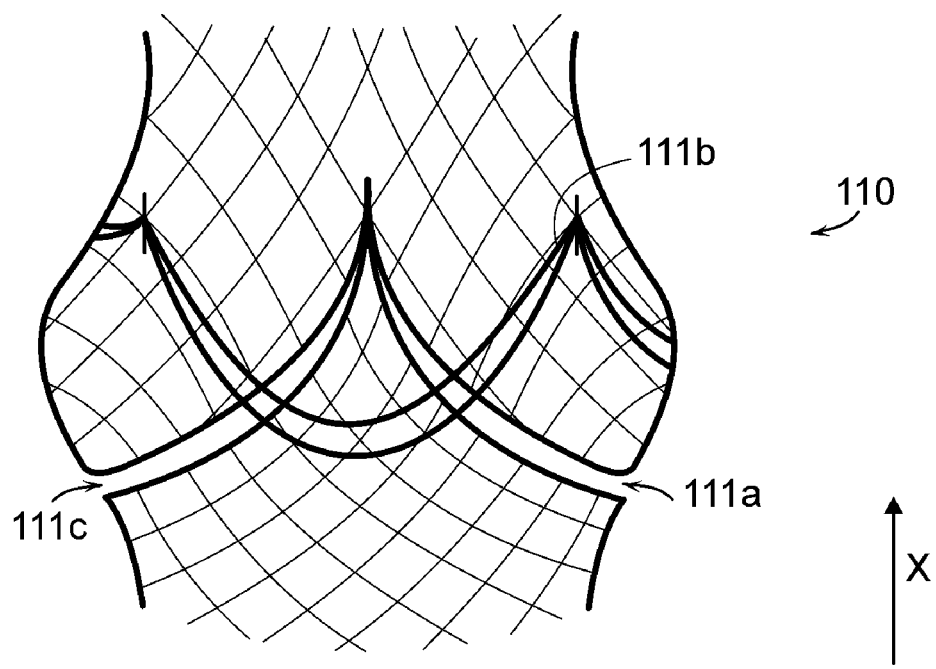
FIG. 11B is a side-view of the valve assembly of FIG. 11A.

In another embodiment, as illustrated in FIGS. 11A and 11B, a valve assembly 110 according to the invention is a unitary body that comprises the functionality of both a stent, such as the stent 30 of FIG. 3B, and a valve frame, such as the valve frame 40 of FIG. 4B. The valve assembly 110 is constructed from a mesh 112. The mesh 112 is constructed from, for example, wires or strips of shape memory material as previously described herein.

Figure 11C:
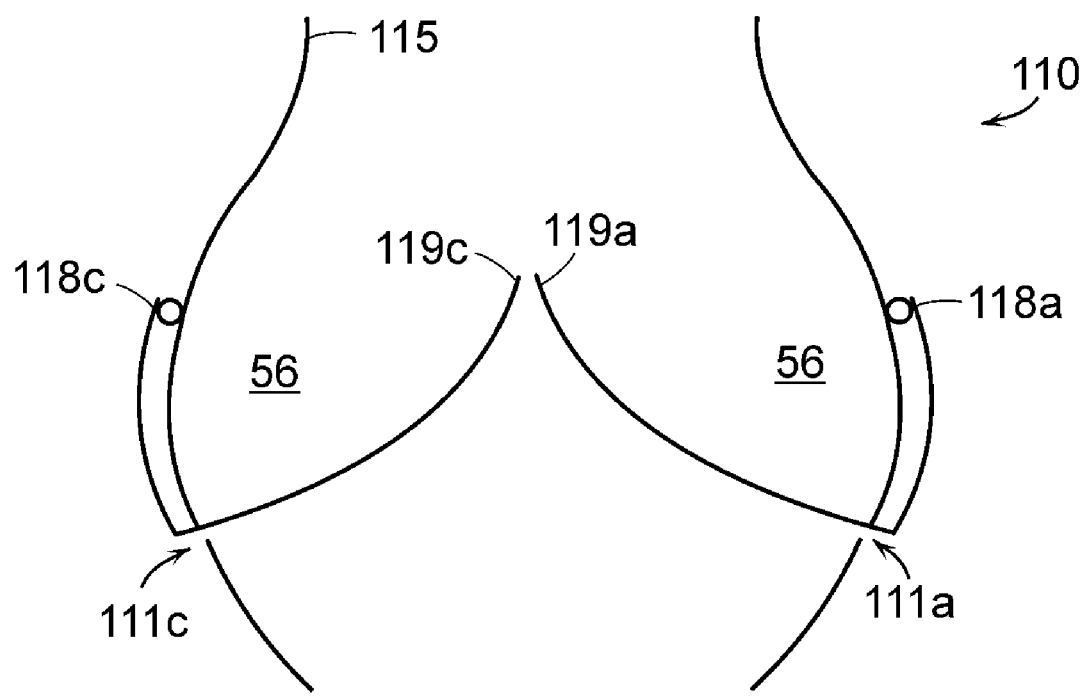
FIG. 11C is a cross-sectional view of the valve assembly of FIG. 11B with a cover material applied to the valve assembly.

Referring now to FIGS. 11A, 11B and 11C, the valve assembly 110 has three valve gaps 111a, 111b and 111c which each act as a hinge point for a cover material, for example, the cover material 56 of FIG. 5C. Valve gap 111b is shown in hidden view in FIG. 11B for clarity of illustration purposes.

The cover material 56 could be a biocompatible material, such as, silicon rubber or bovine, porcine or human tissue that is chemically treated to minimize the likelihood of rejection by the patient's immune system. The cover material 56 is not shown in FIG. 11B for clarity of illustration purposes. The cover material 56 would be applied to the valve assembly 110 prior to deployment of the valve assembly 110 into the body. The cover material could be, for example, sutured to the valve assembly 110 in a location 118a, 118b and 118c (118b is not shown for clarity of illustration purposes). Subsequent to placement of the valve assembly 110 within the body, the cover material 56 is capable of, generally, permitting the flow of blood in the positive direction along the X-axis, as previously described herein.

The valve assembly 110 is capable of being compressed as described previously herein and loaded into an introducing catheter, such as the introducing catheter 61 of FIG. 6. Subsequent to insertion of the introducing catheter 61 into the heart of a patient and locating the introducing catheter 61 in a desirable location, an operator deploys the valve assembly 110 from the introducing catheter 61. The valve assembly 110 then expands because the introducing catheter 61 no longer applies a constraining force to the valve assembly 110. Alternatively, a balloon, such as the balloon 73 of FIG. 7 could be used, as described previously herein, to expand the valve assembly 110.

The valve assembly 110, alternatively, could be expanded by heating the shape memory material once the valve assembly 110 is located in a desirable location in the heart. The valve assembly could warm due to contact with, for example, heart tissue or blood of the patient.

However, as blood flows in the negative direction along the X-axis the free ends 119a, 119b and 119c (the free end 119b is not shown for clarity of illustration purposes) of the cover material 56 move away from an inner wall 115 of the valve assembly 110. The cover material 56, thereby, generally restricts the flow of blood through the valve assembly 110. In this manner, the valve assembly 110 approximates the functioning of a natural heart valve of the body by preventing the flow of blood along the negative direction along the X-axis.

The valve gaps 111a, 111b and 111c could be of any suitable shape (e.g., leaf shaped, oval shaped or generally polygonal shaped) and any number (e.g., three, four or six) such that depending upon the direction of the flow of blood, the flow of blood is either adequately blocked or permitted by the presence of the cover material 56 located on the valve assembly 110. Additionally, the alternative shapes and number of valve gaps must also allow for the valve assembly to be loaded into and unloaded from an introducing catheter, such as the introducing catheter 61 of FIG. 6.

Figure 14A:
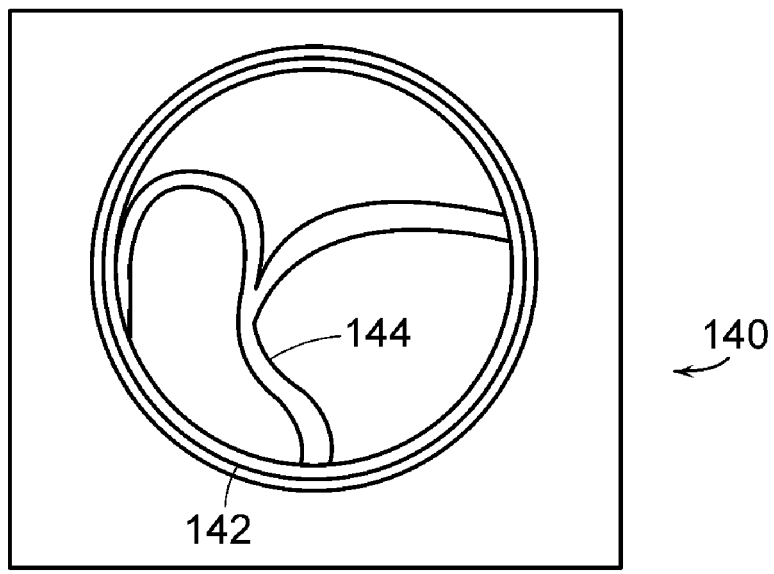
FIG. 14A is a top view of a digital image of a model of a valve assembly, such as the valve assembly of FIG. 11A.
Figure 14B:
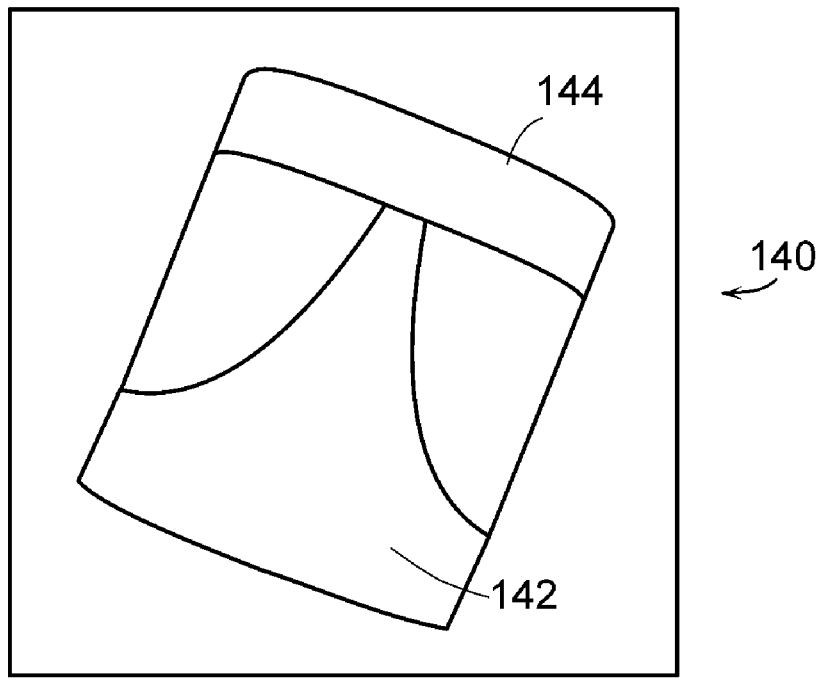
FIG. 14B is a side-view of a digital image of a model of a valve assembly, such as the valve assembly of FIG. 11B.

FIGS. 14A and 14B are digital images of a model 140 of a valve assembly, such as the valve assembly 110 of FIGS. 11A and 11B, respectively. For clarity of illustration purposes the valve assembly model 140 is constructed from a tube 142 and a silicon rubber cover material 144. The valve assembly model 140, referring now to FIG. 14B, is cylindrical in shape. The valve assembly model 140, alternatively, could be any geometric shape as described previously herein.

Figure 12A:
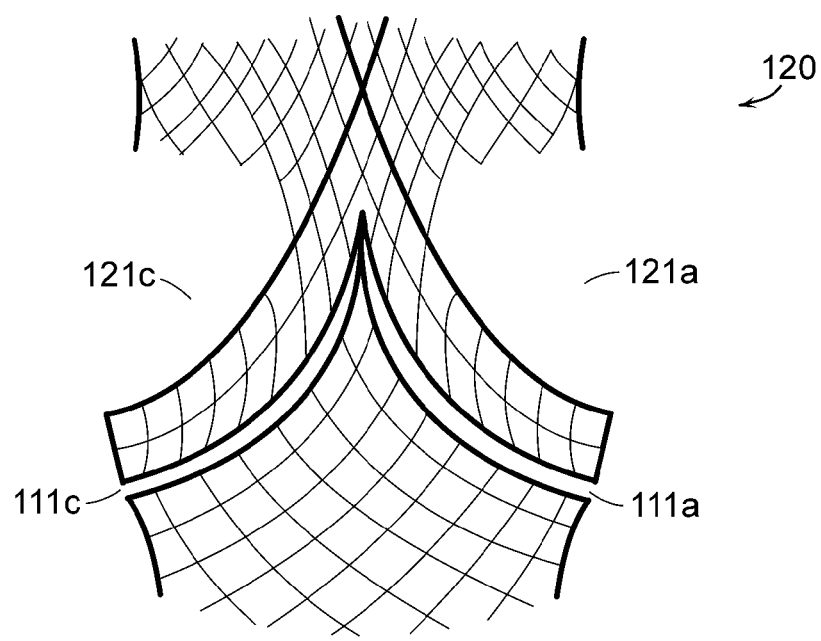
FIG. 12A is a side-view of an embodiment of a valve assembly according to the invention.
Figure 12B:
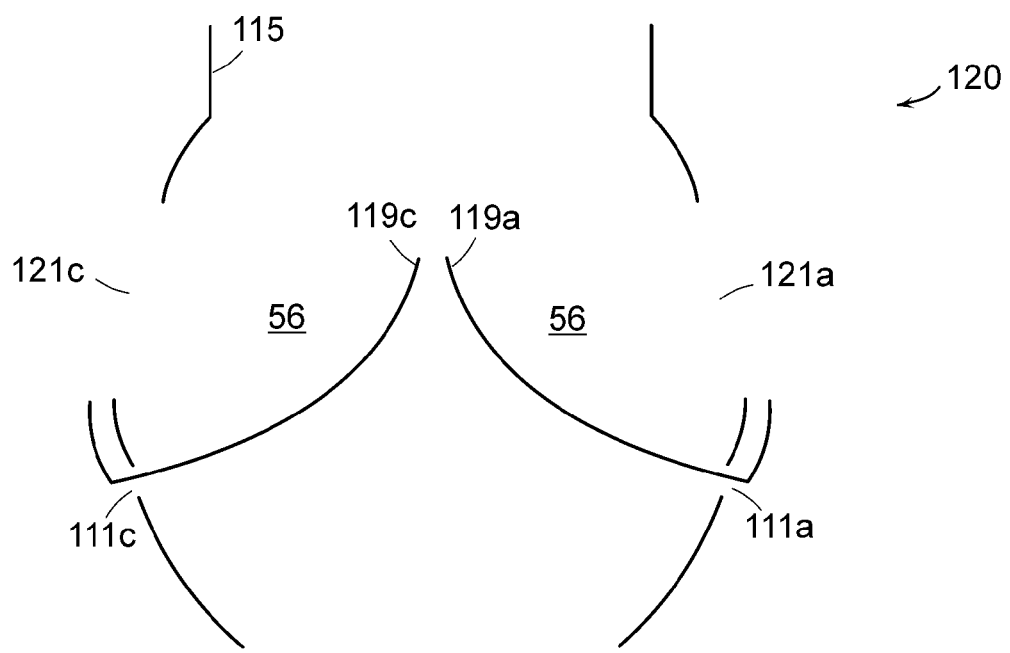
FIG. 12B is a cross-sectional view of the valve assembly of FIG. 12A with a cover material applied to the valve assembly.

In another embodiment, now referring to FIGS. 12A and 12B, a valve assembly 120 has three valve gaps 11a, 11b and 11c (the valve gap 111b is not shown for clarity of illustration purposes). The valve assembly 120 also has two openings 121a and 121c. The openings 121a and 121c, for example, could represent openings in the valve assembly 120 that are in fluid communication with two coronary arteries in the heart. Due to the presence of the valve openings 121a and 121c, less material is required to fabricate the valve assembly 120. As such, it may be possible to use a smaller diameter, introducing catheter, such as the introducing catheter 61 of FIG. 6 to introduce the valve assembly 120 into the heart of the patient.

Figure 15A:
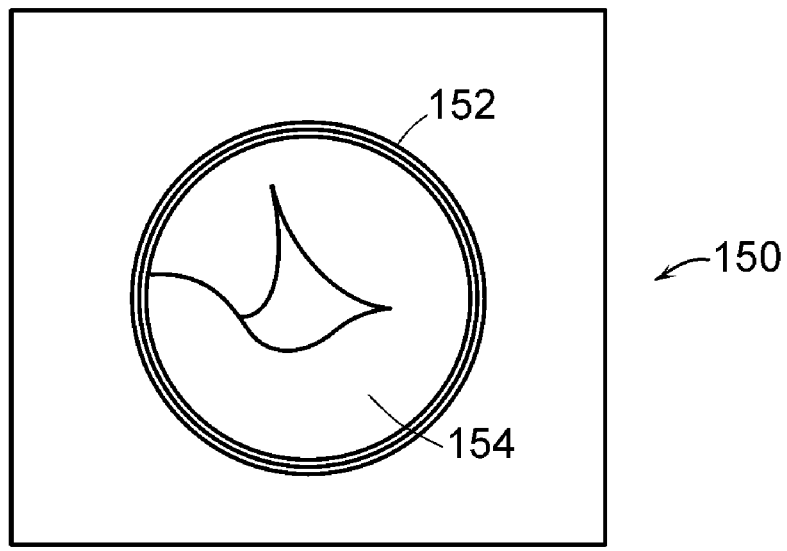
FIG. 15A is a top view of a digital image of a model of a valve assembly, such as the valve assembly of FIG. 12A.
Figure 15B:
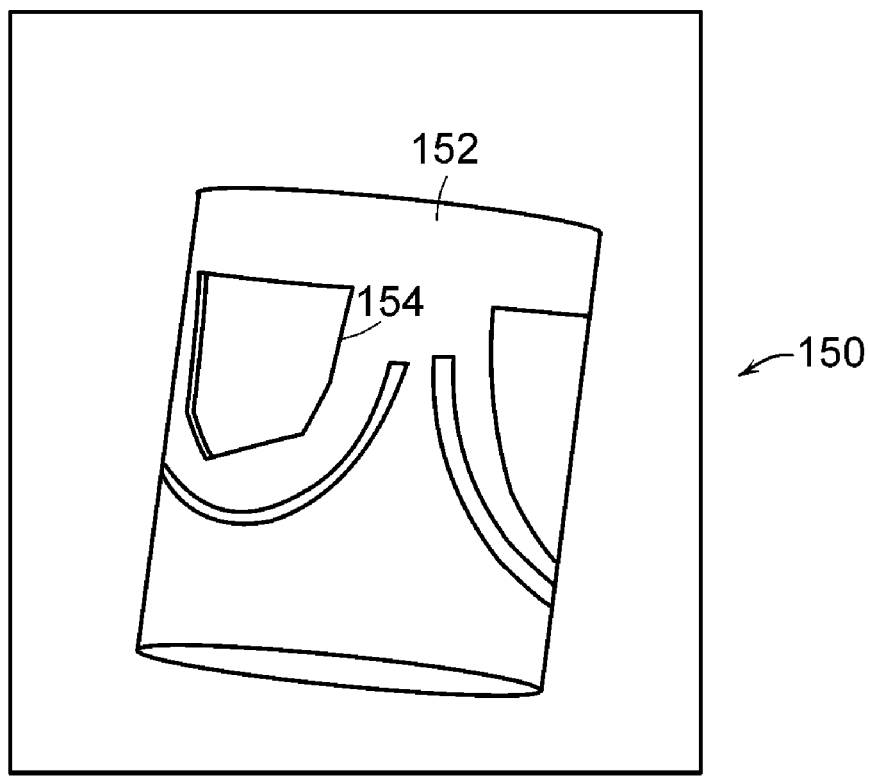
FIG. 15B is a side view of a digital image of a model of a valve assembly, such as the valve assembly of FIG. 12A.

FIGS. 15A and 15B are digital images of a model 150 of a valve assembly, such as the valve assembly 120 of FIG. 12A. For clarity of illustration purposes the valve assembly model 150 is constructed from a tube 152 and a silicon rubber cover material 154. The valve assembly model 150, referring now to FIG. 15B, is cylindrical in shape. The valve assembly model 150, alternatively, could be any geometric shape as described previously herein.

Figure 16:
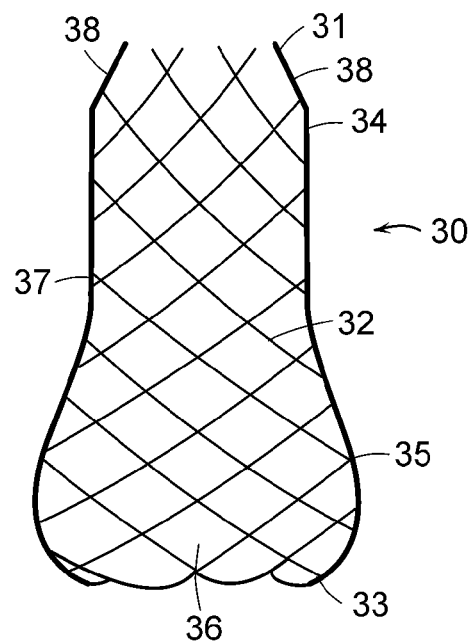
FIG. 16 is a side-view of a stent in accordance with one embodiment of the invention.

As shown in FIG. 16, another embodiment of a stent 30 is illustrated. In this embodiment, the stent 30 approximates the form of a cloverleaf to closely conform, for example, to the cloverleaf-like shape (associated with the three sinuses of a natural heart valve) of the location in a heart where a defective heart valve has been surgically removed. The stent 30 defines a generally cylindrical, elongated body that has a wall 34 that is constructed from a mesh 32. The wall 34 defines a lumen 36. The mesh 32 is constructed from, for example, wires or strips of shape memory material or other alternative materials as earlier described.

Figure 17:
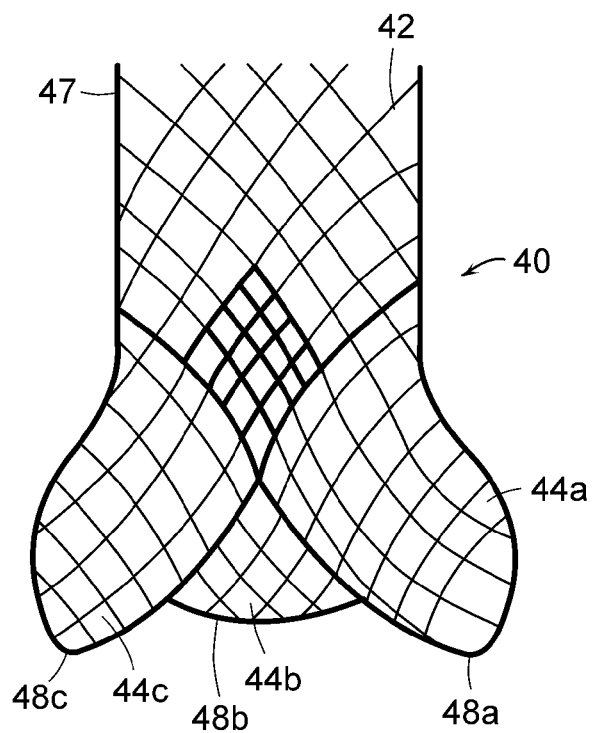
FIG. 17 is a side-view of a valve frame in accordance with one embodiment of the invention.

Referring again to FIG. 16, the lumen 36 of the stent 30 includes a neck portion 37 that can accommodate a partially deployed valve frame 40 (a valve frame 40 is illustrated in FIG. 17). The stent 30 also includes a tapered portion 38 extending from a distal end 31 of the stent 30 and a bulbous portion 35 extending from a proximal end 33 of the stent 30.

Enabling a valve frame 40 to partially deploy within the stent 30 is beneficial, since the valve frame 40 can be repositioned in the stent 30 prior to being fully deployed in the stent 30. Repositioning the valve frame 40 may be necessary, for instance, to ensure a proper alignment of the valve frame 40 within the lumen 36 of the stent 30 so that movement of the valve frame 40 with respect to the stent 30 is minimal once the valve frame 40 is fully deployed.

FIG. 17 illustrates one embodiment of a valve frame 40 in deployed form (i.e., not constrained by, for example, a wall of a lumen of a catheter used to introduce the valve frame 40 into the body). The valve frame 40 may be deployed within a stent, such as the stent 30 of FIG. 16 and can be constructed as described earlier with reference to FIGS. 4A-4B.

Figure 18A:
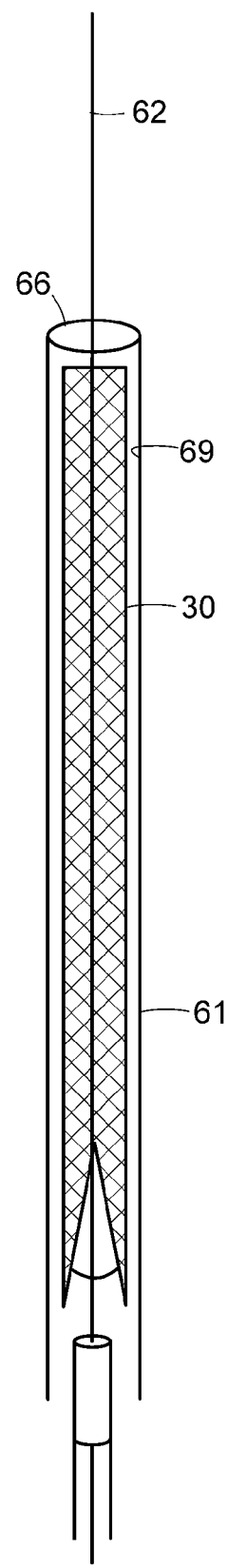
FIGS. 18A-18E are side-views of a valve frame being deployed by catheter into the stent of FIG. 16 in accordance with one embodiment of the invention.
Figure 18B:
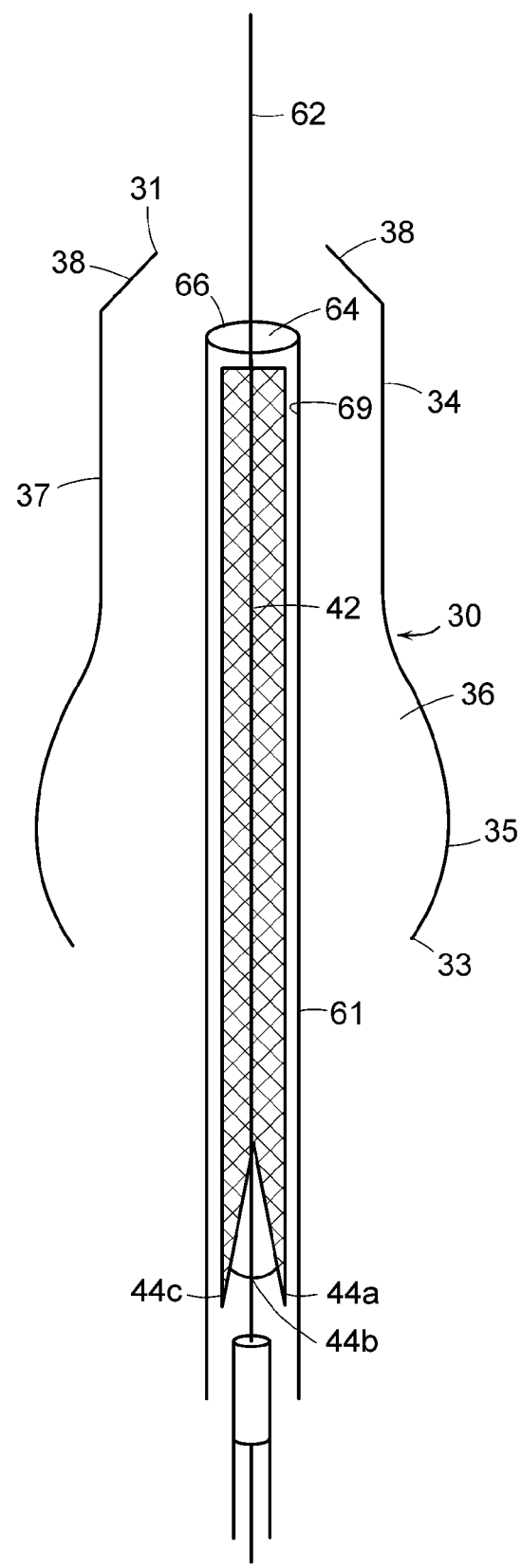
Figure 18C:
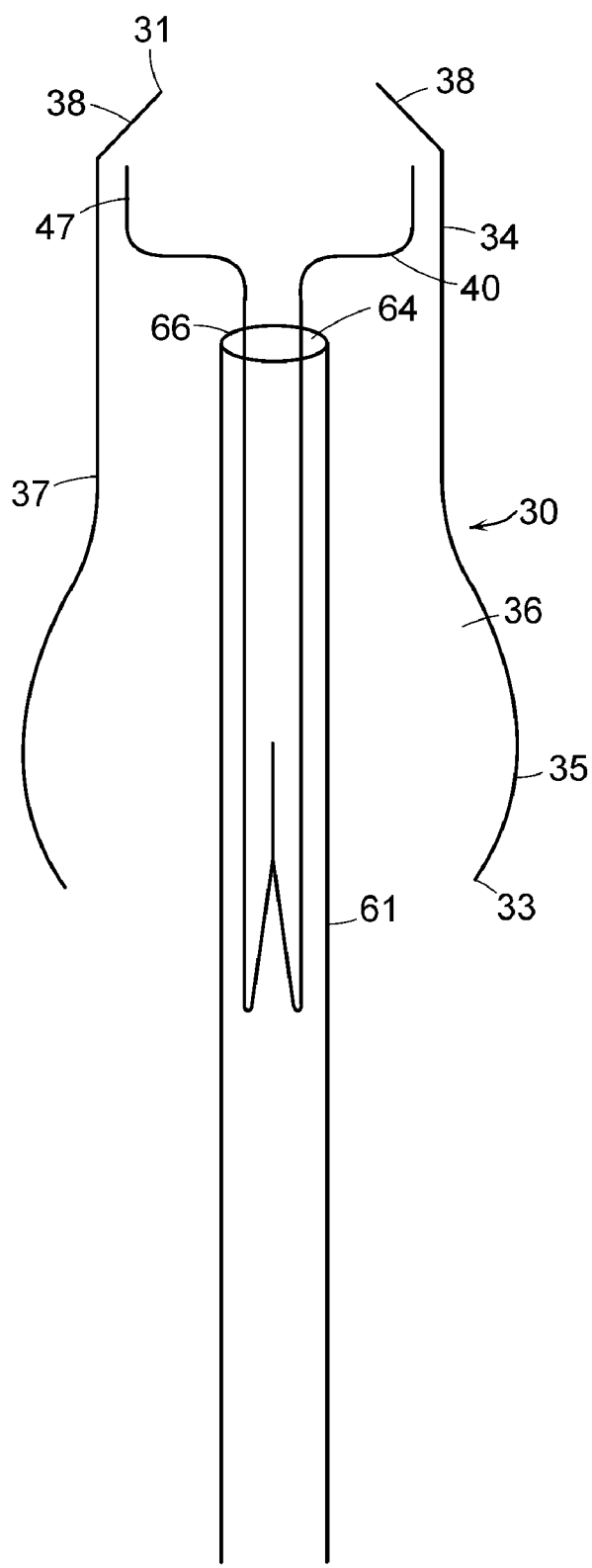
Figure 18D:
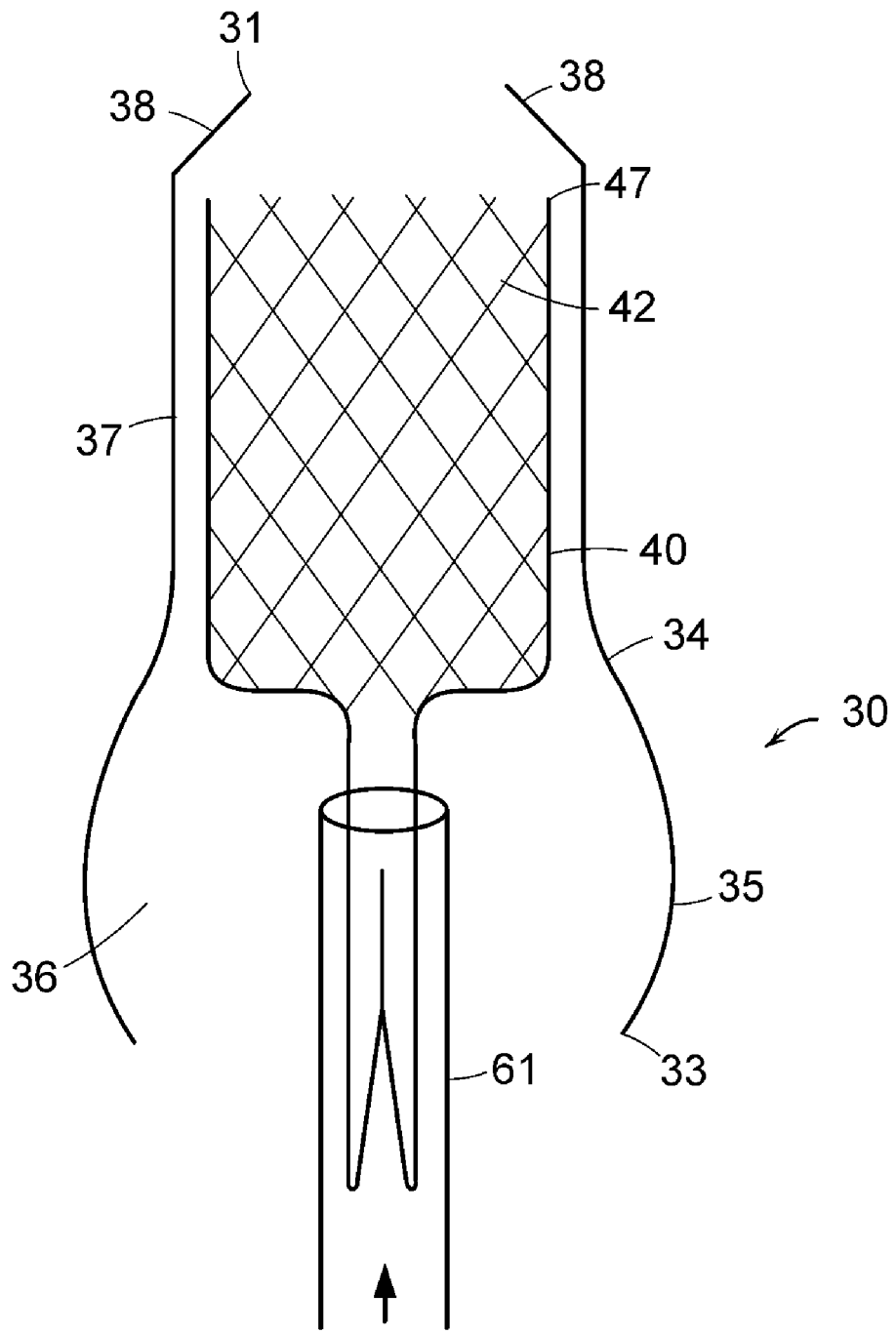
Figure 18E:
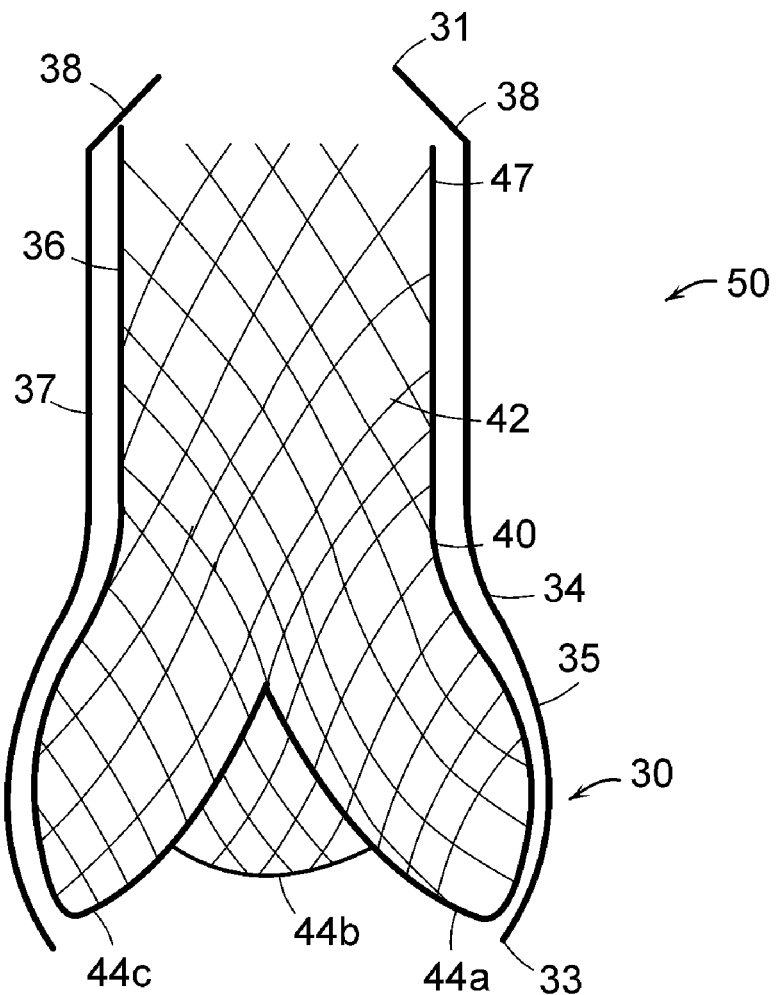
Figure 18E:
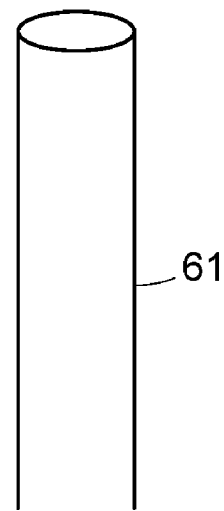

As earlier described, the valve frame 40 may be deployed within the lumen 36 of the stent 30 thereby creating a valve assembly 50 (FIG. 18E). In one embodiment, the valve assembly 50 is deployed within a human heart to replace a natural heart valve that is not functioning properly. The valve frame 40 and the stent 30 are manufactured to ensure that the valve frame 40 maintains a desired (e.g., fixed) placement with respect to the stent 30 when the valve frame 40 and the stent 30 are located within the heart of a patient and subjected to the flow of blood through the valve assembly 50.

In more detail and with reference to FIGS. 18A-18E, method steps associated with introducing an embodiment of the invention into an anatomical lumen are described. As an initial step, with the aid of a fluoroscope, an introducing catheter 61 is delivered via a vessel to the heart by means of a guidewire 62 to a preselected position in an anatomical lumen of the heart. The preselected position may be, for instance, in proximity to the original location of a natural heart valve. The introducing catheter 61 has an inner wall 69 that defines a lumen 64 through which the guidewire 62 is passed. The introducing catheter 61 has an opening 66 out of which the guidewire 62 is extended. In an alternative embodiment, a catheter may be inserted and maneuvered within a patient without the use of a guidewire 62.

With reference to FIG. 18A, the stent 30 is compressed and inserted into the introducing catheter 61, and the stent 30 is guided in a distal direction to the catheter orifice 66 over the guidewire 62. Alternatively, the guidewire 62 may be removed, and the stent 30 may be guided through the introducing catheter 61 to the catheter orifice 66 using the walls 69 of the introducing catheter 61 as a guide.

Once the stent 30 reaches the catheter orifice 66, the stent 30 is guided through the orifice and into the body. The stent 30 may be expanded to a predetermined configuration and size, using methods previously described. The expanded configuration of the stent 30 conforms to a region of the anatomical lumen (not shown) and in one embodiment, the size and shape of the stent 30 is sufficient to hold the stent 30 in a substantially fixed position and orientation within the anatomical lumen. Alternatively, as earlier described, the stent 30 includes elements (e.g., sutures, hooks, spikes or tack tips) that attach to the interior walls of the anatomical lumen so as to more rigidly hold the stent 30 in a fixed position.

Referring to FIG. 18B, after the stent 30 is inserted into the body, the valve frame 40 is compressed and inserted into the introducing catheter 61. Like the stent 30, the valve frame 40 is guided in a distal direction to the catheter orifice 66 over the guidewire. Alternatively, the guidewire 62 may be removed, and the valve frame 40 may be guided through the introducing catheter 61 to the catheter orifice 66 using the walls 69 of the introducing catheter 61 as a guide.

Referring to FIG. 18C, once the valve frame 40 reaches the catheter orifice 66, the valve frame 40 is partially deployed into the neck portion 37 of the elongated lumen 36 of the expanded stent 30. The elongated stent 30 and the elongated body of the valve frame 40 enable the valve frame 40 to be partially deployed in the stent 30. In the partially deployed state, the valve frame 40 may still be retracted into the introducing catheter 61, and re-positioned within the stent 30 if necessary. Upon being partially deployed, a distal end 47 of the valve frame 40 expands and assumes substantially the same size and shape as the lumen 36 of the expanded stent 30. A determination is then made, for example, using fluoroscopy, as to whether the valve frame 40 is properly positioned within the stent 30. To be properly positioned, the distal end 47 of the valve frame should align as shown in FIG. 18C with the tapered portion 38 of the stent 30. If a determination is made that the stent 30 and the valve frame 40 are not in proper alignment, the valve frame 40 can be retracted into the introducing catheter 61, and then re-deployed at the proper location within the stent 30.

Once the valve frame 40 is properly aligned with the stent 30, the user fully releases the valve frame 40 into the stent 30, and withdraws the catheter 61 (FIGS. 18D-18E). When the valve frame 40 is fully deployed within the stent 30, the valve frame 40 expands, and adjusts to substantially correspond with the shape of the stent 30, such that the outer surfaces of the valve frame 40 mate with the inner surfaces of the stent 30. The mating surfaces of the valve frame 40 and the stent 30 maintain the positioning of the valve frame 40 within the stent 30. For example, the distal end 47 of the valve frame 40 engages with tapered portion 38 of the stent 30, and the valve members 44a, 44b, and 44c expand to engage the bulbous portion 35 of the stent 30.

Figure 19A:
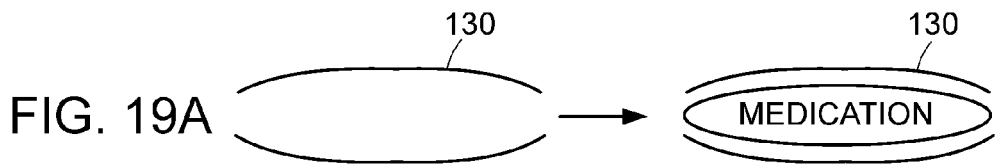
FIGS. 19A-19E are side-views of docking stations for receiving medical devices or drugs.
Figure 19B:
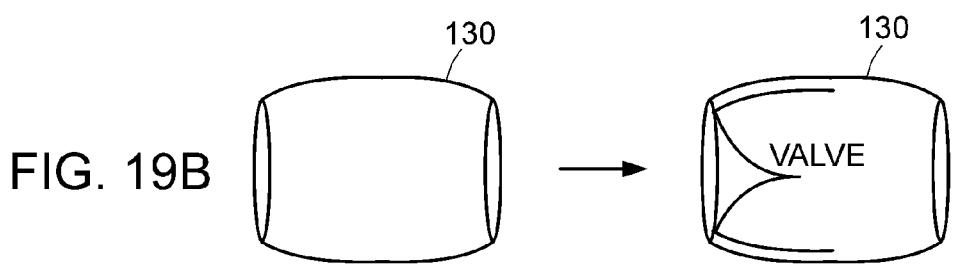
Figure 19C:
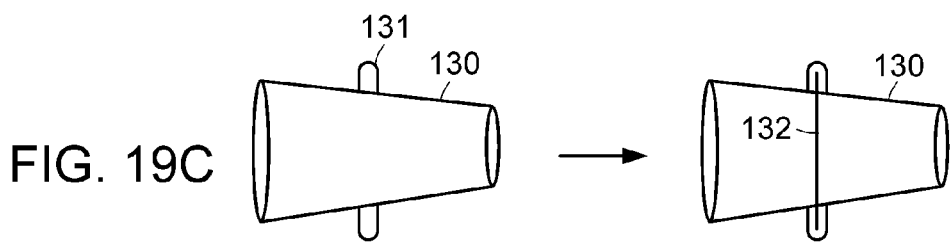
Figure 19D:
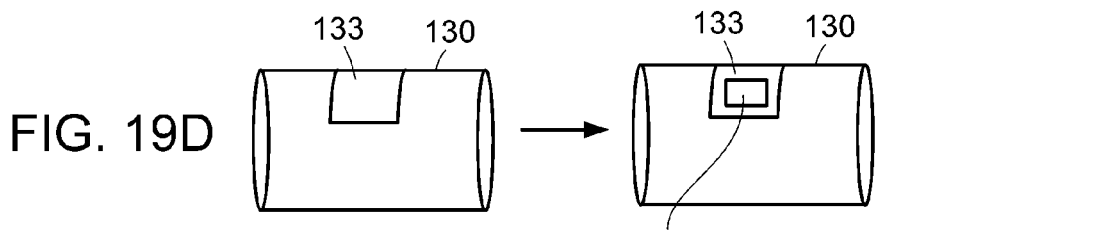
Figure 19E:
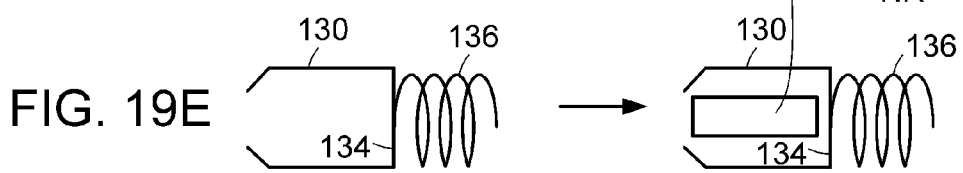

Referring to FIGS. 19A-19E, in other embodiments, the stent/docking station 130 may be any geometric shape (e.g., cylindrical, conical, spherical or barrel-like) that is compatible with the placement of the docking station 130 within, for example, a lumen of the heart or in a ureter. The illustrated docking stations 130 may be made from the stent materials described earlier. The docking stations 130 when inserted into the body may hold a variety of devices in addition to valves. For example, referring to FIG. 19A, the docking station 130 includes a pocket that receives a capsule of medicine. The capsule may be held in place by frictional engagement with the docking station 130. For example, dimples may protrude inwardly from the inner surface of the docking station 130 to engage the capsule. Referring to FIG. 19C, in another embodiment, the docking station 130 includes an external annular ring 131 that may hold a pressure responsive valve and/or sphincter 132 to reduce the flow of fluids in a body cavity. In another embodiment as illustrated in FIG. 19D, the docking station 130 includes a recessed surface or cavity 133 that may hold a monitoring device, such as a video camera or heart rate monitor. Referring to FIG. 19E, the docking station 130, in one embodiment, forms a closed body to receive a medical device, drug, or radiation source. In one embodiment, the drug is a slow release medication formulation. The closed end 134 of the docking station 130 may be coupled to a mounting device 136 that is used to secure the docking station 130 in the body.

Figure 20A:
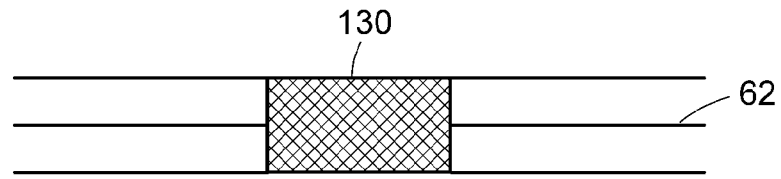
FIGS. 20A-20F are side-views of docking stations inserted into the body at various locations.
Figure 20C:
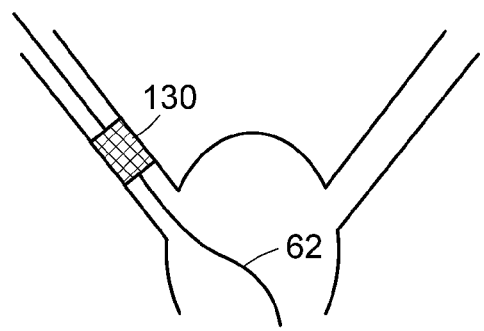
Figure 20B:
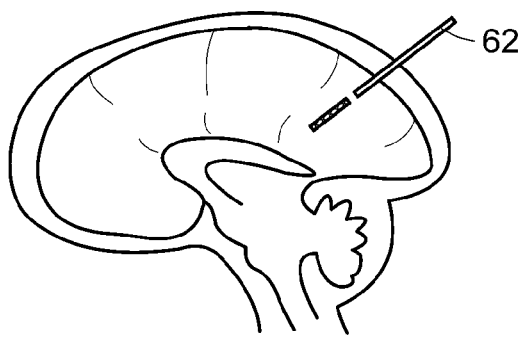
Figure 20D:
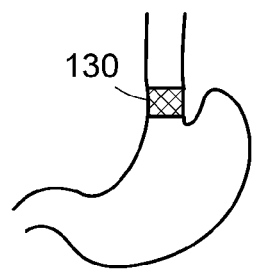
Figure 20F:
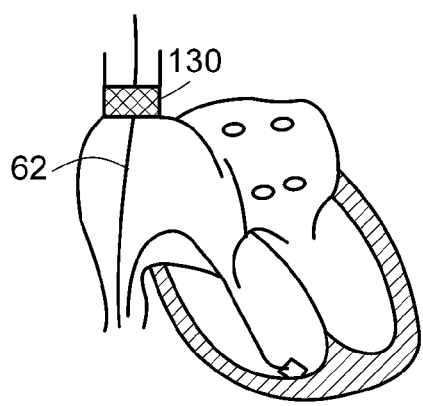
Figure 20E:
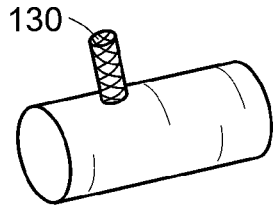

Referring to FIGS. 20A-20F, the docking station 130 is shown inserted into various locations of the body including a blood vessel (FIG. 20A), the brain (FIG. 20B), a ureter (FIG. 20C), the stomach (FIG. 20D), the colon (FIG. 20E), and the heart (FIG. 20F). In general, the docking station 130 may be inserted into any cavity, organ, vessel, valve, sphincter, or lumen of the body. The docking station 130 may be inserted through a catheter, as described above with reference to FIGS. 18A-18E. Once the docking station 130 is placed in the body, the docking station 130 may receive medical devices that either temporarily or permanently couple with the docking station 130 as described above. As an example, as illustrated in FIG. 20B, a drug/radiation source may be inserted into a docking station 130 located in the brain to treat a seizure focus, a malignancy, or to repair damaged tissue. Alternatively, referring to FIGS. 20C and 20D, a docking station 130 mounted in the stomach or a ureter may couple to a pressure responsive valve and/or sphincter (FIG. 19C) to prevent reflux. Referring to FIG. 20E, in another embodiment, a docking station 130 similar to the docking station 130 illustrated in FIG. 19D may be inserted into the colon. The docking station 130 may then receive a monitoring device to provide feedback to care providers. Referring to FIG. 20F, as another example, a heart rate monitor, an electrocardiogram sensor, or a pacemaker may be coupled to a docking station 130 implanted in the heart. One advantage of the current invention is that if a medical device or a drug is no longer required, the medical device or drug may be removed from the docking station 130, with the docking station 130 remaining in place within the body for future use with another medical device or drug.

In another embodiment (FIG. 21) the replacement valve assembly 310 includes a stent 330 and valve frame 340. The stent 330 is expandable between a first compressed state (shown) and a second expanded state (not shown). The stent 330 has a cylindrical body constructed from a plurality of serpentine wires (generally 331). Each of the serpentine curves of a first wire 331 is attached at the vertices 333 to each of the serpentine curves of an adjacent wire 331. In one embodiment the wires 331 are constructed of stainless steel. At each end of the stent 330 is an additional serpentine shaped end wire (generally 334) having serpentine curves of smaller radius. Several of the vertices of each of these serpentine end wires 334 are attached to several of the vertices 336 other serpentine wires 331 of the body.

Figure 22:
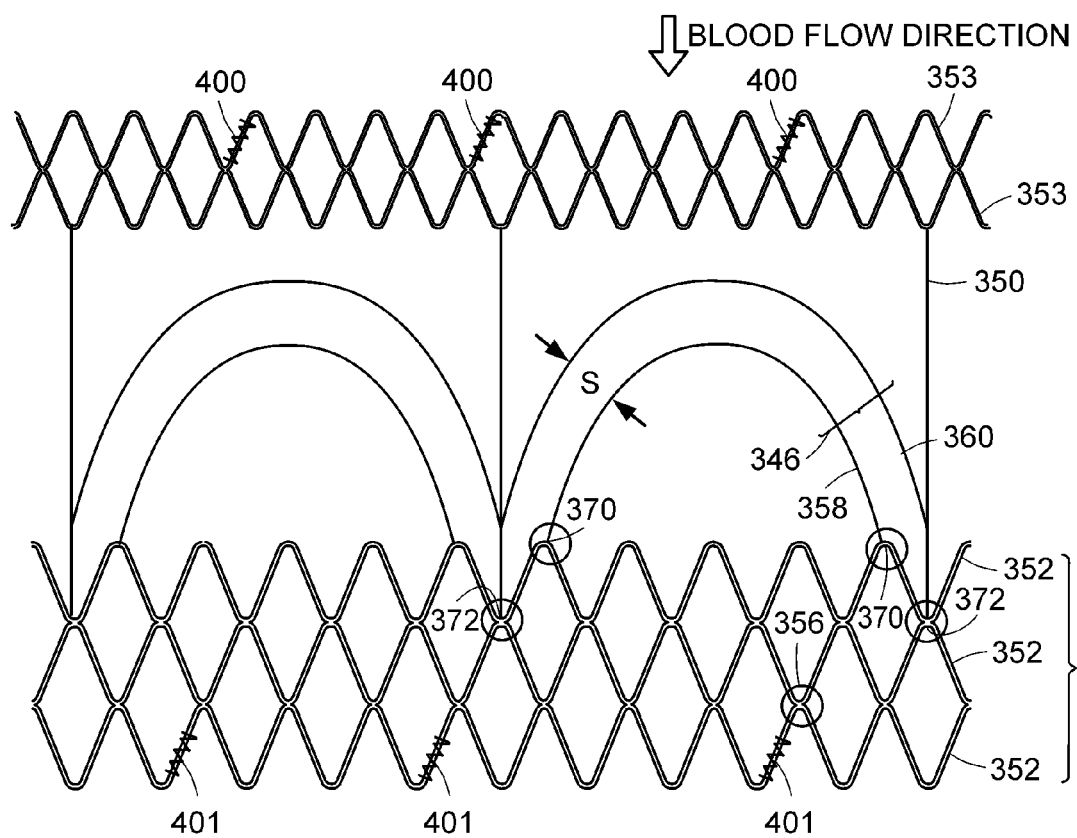
FIG. 22 is an opened view of a portion of another embodiment of the valve frame (without leaflets) of the invention.

Referring also to FIG. 22, the valve frame 340 includes a substantially cylindrical body portion 341, a plurality of valve attachment pairs 346, and optionally a plurality of standoffs 350 attached to one or more exterior serpentine wire rings 353.

The substantially cylindrical body portion 341 of the valve frame 340 is constructed of a plurality of serpentine curved wires 352. Each of the vertices 356 of the serpentine curves of a first wire 352 is attached at the vertices 356 to each of the vertices of the serpentine curves of an adjacent wire 352. In one embodiment the wires 352 are constructed of Nitinol. Again the substantially cylindrical body portion 341 is expandable between a first compressed state (not shown) and a second expanded state (shown). It should be noted that when the terms vertex or trough are used, the convention is that the word trough is a bend in the wire that points in the direction of blood flow and a vertex is a bend that points in a direction opposite blood flow.

Figure 21:
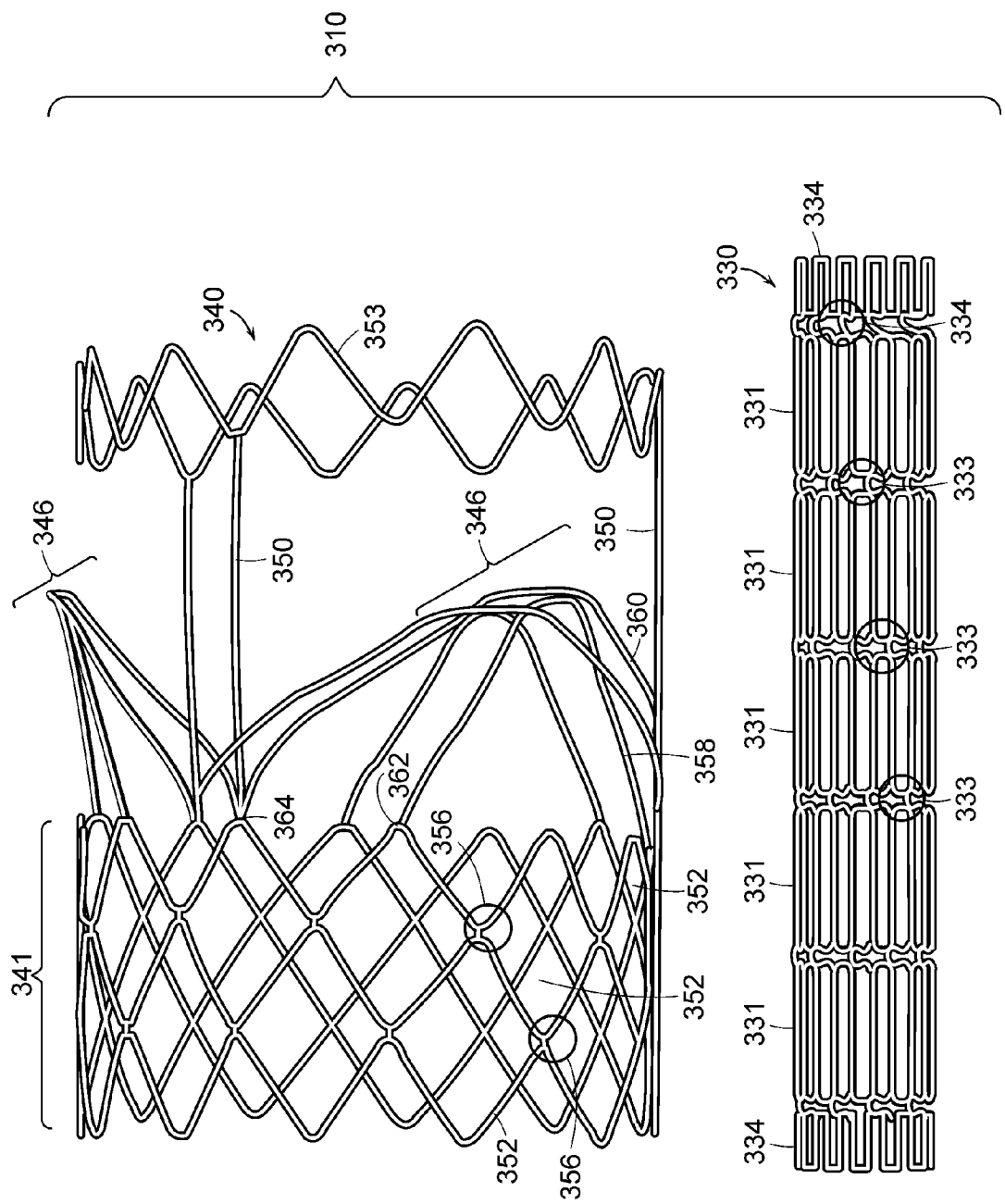
FIG. 21 is a view of an embodiment of the stent and the valve frame (without) leaflets) of the invention.

At one end of the cylindrical body 341 of the valve frame 340 are three sets of valve attachment pairs 346. Each valve attachment pair 346 includes an inner curved wire 358 and an outer curved wire 360. Each curved wire 358, 360 is attached either to a vertex 362, 364 (respectively as shown in FIG. 21) or to a trough 372 and vertex 370 (respectively as shown in FIG. 22). In one embodiment, (FIG. 22) the space S between the inner curved wire 358 and the outer curved wire 360 is substantially parabolic and constant.

Figure 23:
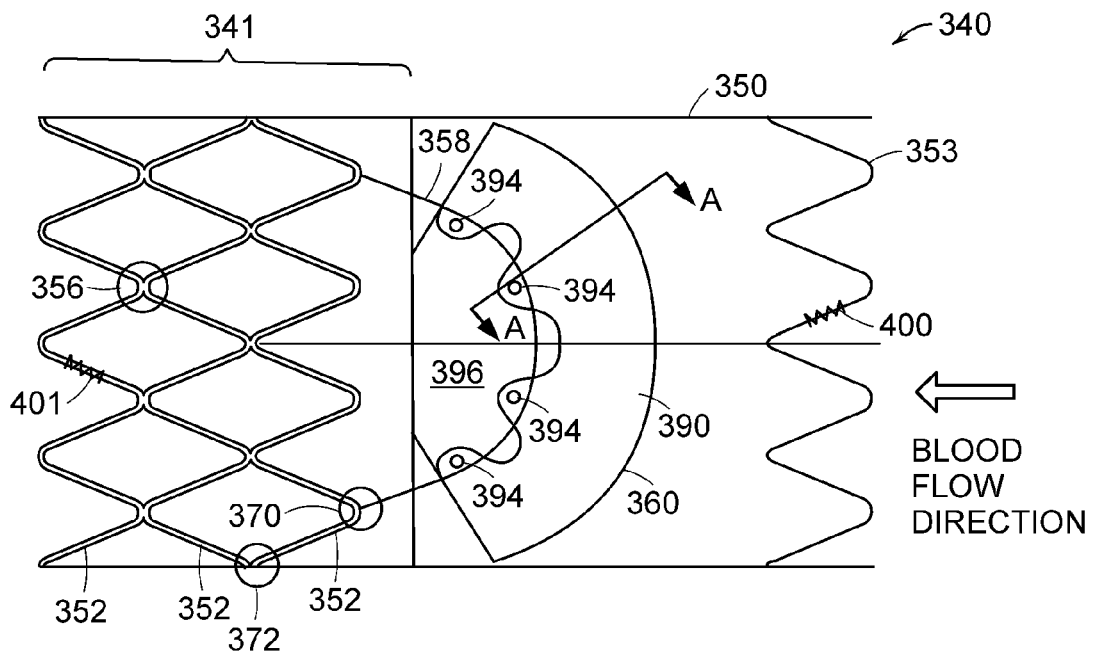
FIG. 23 is a plan view of the embodiment of the valve frame of FIG. 22 with leaflets attached.
Figure 24:
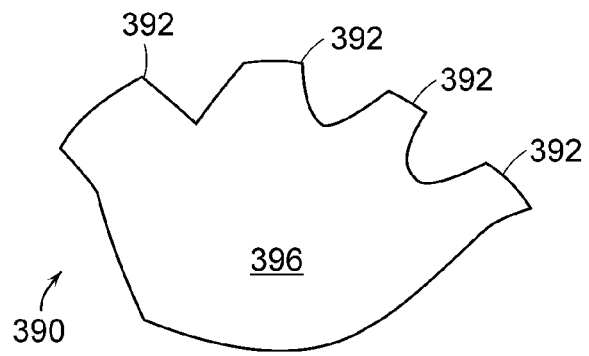
FIG. 24 is a plan view of a leaflet.
Figure 25:
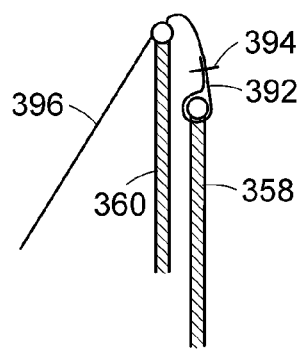
FIG. 25 is a cross-sectional view through line AA' of FIG. 23 showing the attachment of the leaflet to the inner curved wire and the placement of the leaflet over the outer curved wire.

To each valve attachment pair 346 is attached a leaflet 390 (FIGS. 23, 24 and 25). Each leaflet 390 has a leaflet body 396 and a plurality of leaflet projections 392. When attached to the valve frame 340, the leaflet body 396 is located within the lumen of the valve frame 340. Referring to FIG. 25, the leaflet 390 is positioned such that the portion of the leaflet body 396 nearest the projections 392 is pulled over the outer curved wire 360 and the leaflet projections 392 are curved over the inner curved wire 358. Each leaflet projection 392 is attached by sutures 394 to itself. This anchors the leaflet projection 392 to the inner curved wire 358 and permits the leaflet body 396 to be secured and maintain its shape within the lumen of the valve frame 340. This configuration prevents the sutures 394 from being exposed to blood passing through the valve and provides free motion of the leaflet body without any contact to prosthetic materials thereby preventing damage to the leaflet.

Further, by placing the attachment of the outer 360 and inner 358 curved wires to the body 341 of the valve frame 340, at adjacent vertices 370 and troughs 372, the distance between the inner 358 and outer 360 curved wires is substantially assured. As a result, the movement of the valve leaflets 390 does not cause the curved wires 358, 360 to touch, thereby preventing damage to the leaflets 390.

In one embodiment an optional plurality of standoffs 350 hold one or more exterior serpentine rings 353 at a distance away from the outer curved wire 360 to provide extra support to the valve frame 340. At several locations on the exterior serpentine ring(s) 353 are located platinum markers 400. In one embodiment (shown) platinum wire is wrapped about the exterior serpentine ring(s) 353 in several locations. These locations then serve as radiopaque markers 400 to help position the valve frame 340 within the stent 330. In another embodiment the platinum markers are also positioned on the opposite end of the valve frame so that both ends of the valve frame 340 can be seen clearly under fluoroscopy as the valve frame 340 is positioned within the stent 330. Each standoff 350 must be long enough so that when the valve frame 340 is compressed to fit within a catheter, the leaflet 396 which is turned over the outer wire 360 does not contact the exterior serpentine ring 353 thereby potentially causing damage to the leaflet 390.

Figure 26:
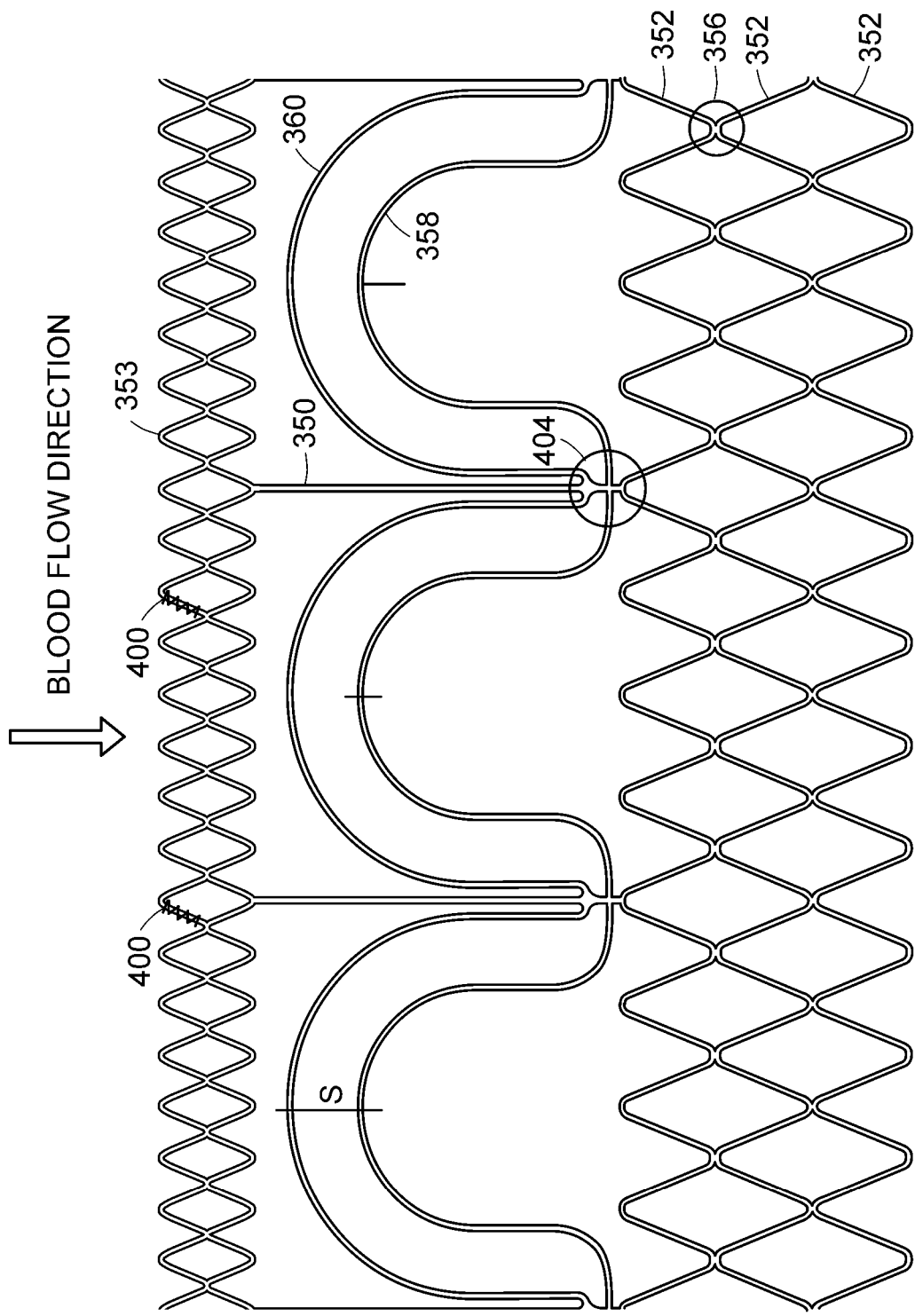
FIG. 26 is an opened view of a portion of another embodiment of the valve frame (without leaflets) of the invention.

FIG. 26 depicts a similar valve frame but one in which the inner 358 and outer 360 curved wires are attached to the same location 404 on vertices of wire 352 of the cylindrical body 352.

In use, the stent 330 is inserted into position in the heart through a catheter as described previously with respect to other embodiments. An elongate balloon is introduced through a catheter into the lumen of the stent 330. The balloon is inflated within the stent 330 and the stent 330 expands radially substantially uniformly along its length. Then a substantially spherical balloon is introduced into middle the expanded stent 330 and inflated. This additional inflation causes the center region of the stent 330 to expand further causing the stent 330 to take on a barrel shape.

Next the compressed valve frame 340 with attached leaflets 396 is introduced into the stent 330 through a catheter and permitted to expand. The tapered ends of the barrel shape of the stent 330 holds the valve frame 340 in place even when the closed valve results in pressure being placed on the valve frame 340 due to the stopped blood flow.

Other embodiments incorporating the concepts disclosed herein may be used without departing from the spirit and scope of the invention. The described embodiments are to be considered in all respects as only illustrative and not restrictive.

What is claimed is:

1. A replacement heart valve comprising:
a valve frame comprising a body defining a lumen, wherein the body of the valve frame comprises:
   a substantially cylindrical body portion, wherein one end of the substantially cylindrical body portion comprises a serpentine edge comprising a plurality of troughs and vertices;
   one or more exterior serpentine rings at a distance away from the substantially cylindrical body portion;
   a plurality of valve attachment wires between the one or more exterior serpentine rings and the substantially cylindrical body portion, the plurality of valve attachment wires comprising a plurality of curved wire pairs, wherein each curved wire pair comprises an inner curved wire and an outer curved wire; and
   a plurality of standoff wires attached to the one or more exterior serpentine rings and the substantially cylindrical body portion; and
   a plurality of valve leaflets attached to the valve attachment wires;
wherein the ends of each inner curved wire is attached to spaced apart vertices of the serpentine edge, and the ends of each outer curved wire is attached to spaced apart troughs of the serpentine edge, wherein the serpentine edge is constructed and arranged such that, in use, each vertex points to a direction opposite blood flow, and each trough points to the direction of blood flow.

2. The replacement heart valve of claim 1, wherein the inner curved wire and the outer curved wire are separate from each other by a space that is substantially constant.

3. The replacement heart valve of claim 1, wherein the inner curved wire and the outer curved wire are parabolic in curvature.

4. The replacement heart valve of claim 1, wherein each valve leaflet comprises a leaflet body and one or more leaflet projections, wherein the one or more leaflet projections are curved around a respective inner wire and attached to itself, and the leaflet body extends over a respective outer curved wire.

5. The replacement heart valve of claim 4, wherein each leaflet is positioned such that the leaflet body is located within the lumen of the valve frame, the portion of the leaflet body nearest the one or more leaflet projections is pulled away from the lumen over a respective outer curved wire and toward a respective inner curved wire to position the one or more leaflet projections such that they are extended toward the lumen and curved around the respective inner curved wire.

6. The replacement heart valve of claim 1, comprising one or more radiopaque markers at the one or more exterior serpentine rings.

7. The replacement heart valve of claim 1, comprising one or more radiopaque markers at the substantially cylindrical body portion.

8. The replacement heart valve of claim 1, wherein the substantially cylindrical body portion is constructed of a plurality of serpentine curved wires.

9. The replacement heart valve of claim 8, wherein each serpentine curved wire is composed of nickel-titanium.

10. The replacement heart valve of claim 1, wherein each standoff wire is sufficiently long to prevent contact between the valve leaflets and the exterior serpentine rings when the valve frame is in a compressed state.

* * * * *